(12) United States Patent
Klassen et al.

(10) Patent No.: US 10,835,527 B2
(45) Date of Patent: *Nov. 17, 2020

(54) COMPOSITIONS AND METHODS FOR REDUCING MAJOR ADVERSE CARDIOVASCULAR EVENTS

(71) Applicant: Nalpropion Pharmaceuticals LLC, Morristown, NJ (US)

(72) Inventors: Preston Klassen, La Jolla, CA (US); Kristin Taylor, San Diego, CA (US)

(73) Assignee: Nalpropion Pharmaceuticals LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/356,663

(22) Filed: Mar. 18, 2019

(65) Prior Publication Data

US 2019/0314363 A1    Oct. 17, 2019

Related U.S. Application Data

(63) Continuation of application No. 15/101,878, filed as application No. PCT/US2014/068527 on Dec. 4, 2014, now Pat. No. 10,231,962, which is a continuation of application No. 14/322,810, filed on Jul. 2, 2014, now Pat. No. 8,969,371.

(60) Provisional application No. 61/913,216, filed on Dec. 6, 2013, provisional application No. 61/914,938, filed on Dec. 11, 2013, provisional application No. 61/984,580, filed on Apr. 25, 2014.

(51) Int. Cl.
*A61K 31/485* (2006.01)
*A61P 3/04* (2006.01)
*A61K 31/137* (2006.01)

(52) U.S. Cl.
CPC .......... *A61K 31/485* (2013.01); *A61K 31/137* (2013.01)

(58) Field of Classification Search
CPC . A61K 2300/00; A61K 31/137; A61K 31/485
See application file for complete search history.

(56) References Cited

PUBLICATIONS

A Multicenter, Randomized, Double-Blind, Placebo-Controlled Study Assessing the Occurrence of Major Adverse Cardiovascular Events (MACE) in Overweight and Obese Subjects With Cardiovascular Risk Factors Receiving Naltrexone SR/Bupropion SR: Clinical Trials Identifier. NCT01601704' by ClinicalTrials.gov Archive , 0.*

* cited by examiner

*Primary Examiner* — Savitha M Rao
(74) *Attorney, Agent, or Firm* — Servilla Whitney LLC

(57) ABSTRACT

The present application relates to compositions, kits, uses, systems and methods of using naltrexone and bupropion, or pharmaceutically acceptable salts thereof, for reducing the risk of adverse cardiovascular outcomes or events, including Major Adverse Cardiovascular Events (MACE) in subjects, preferably those at increased risk of adverse cardiovascular outcomes or MACE, that may be overweight or obese. The present application also relates to compositions, kits, uses, systems and methods of using naltrexone and bupropion or pharmaceutically acceptable salts thereof for treatment of overweight or obesity in subjects, preferably at increased risk of adverse cardiovascular outcomes or MACE, wherein the treatment reduces the risk of MACE.

20 Claims, 11 Drawing Sheets

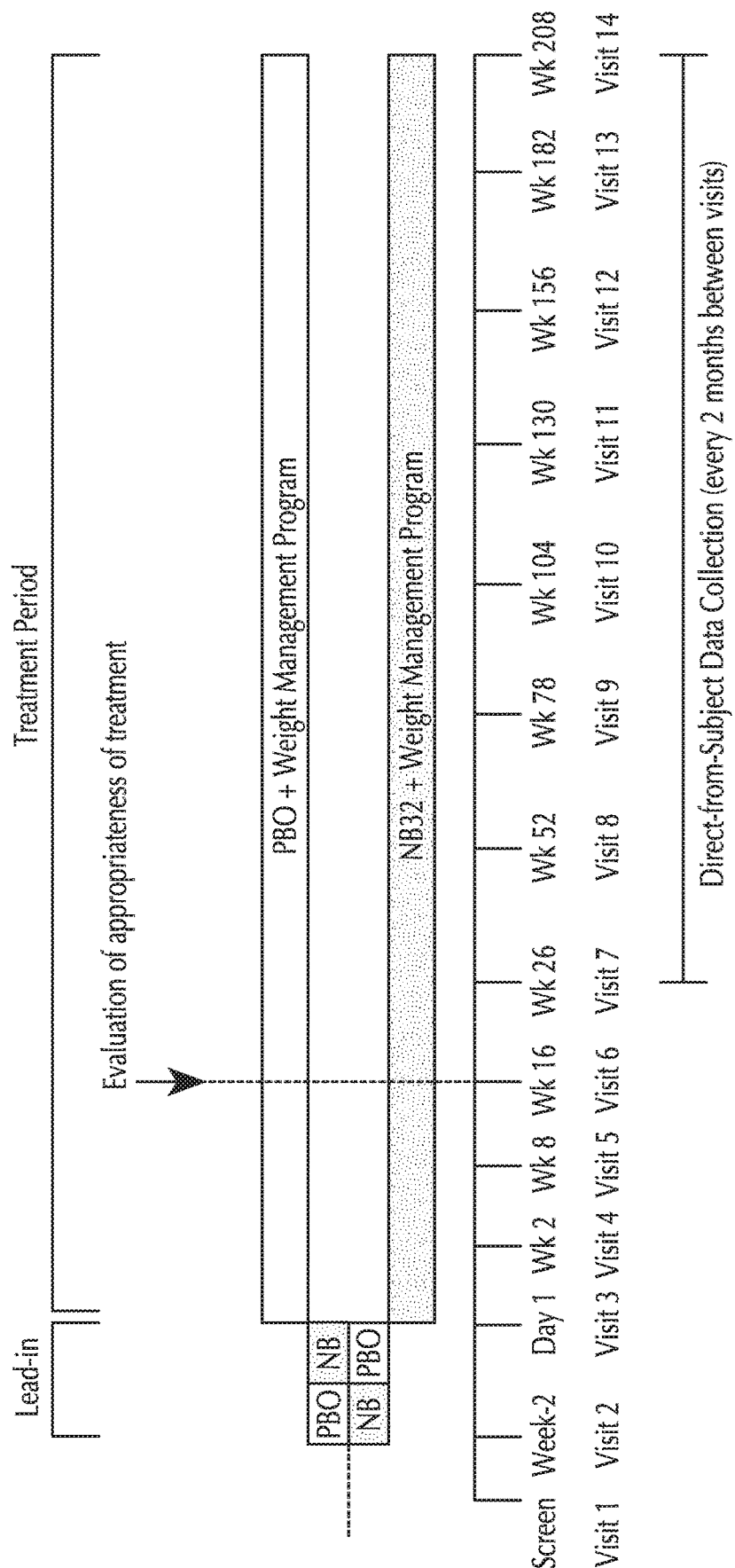

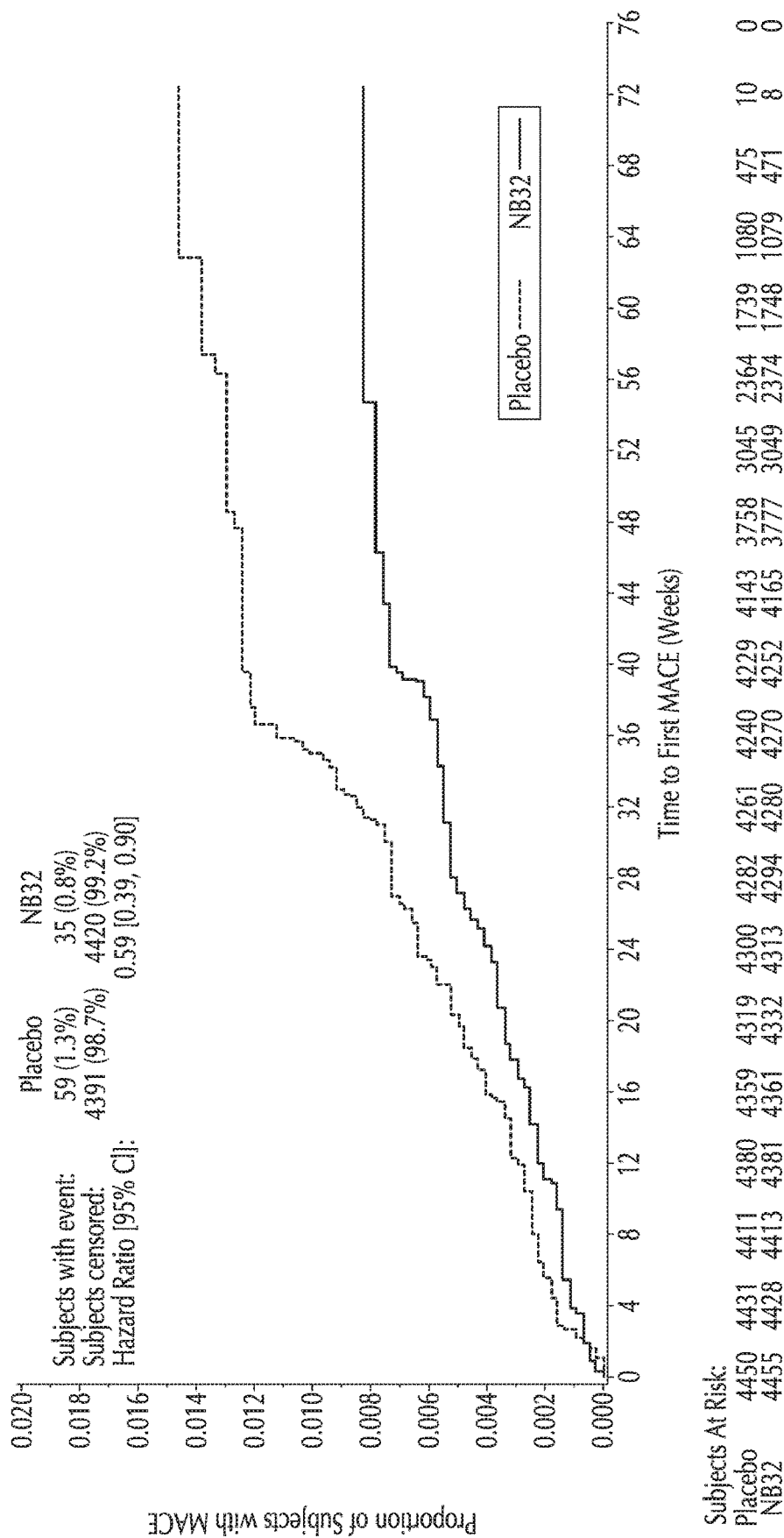

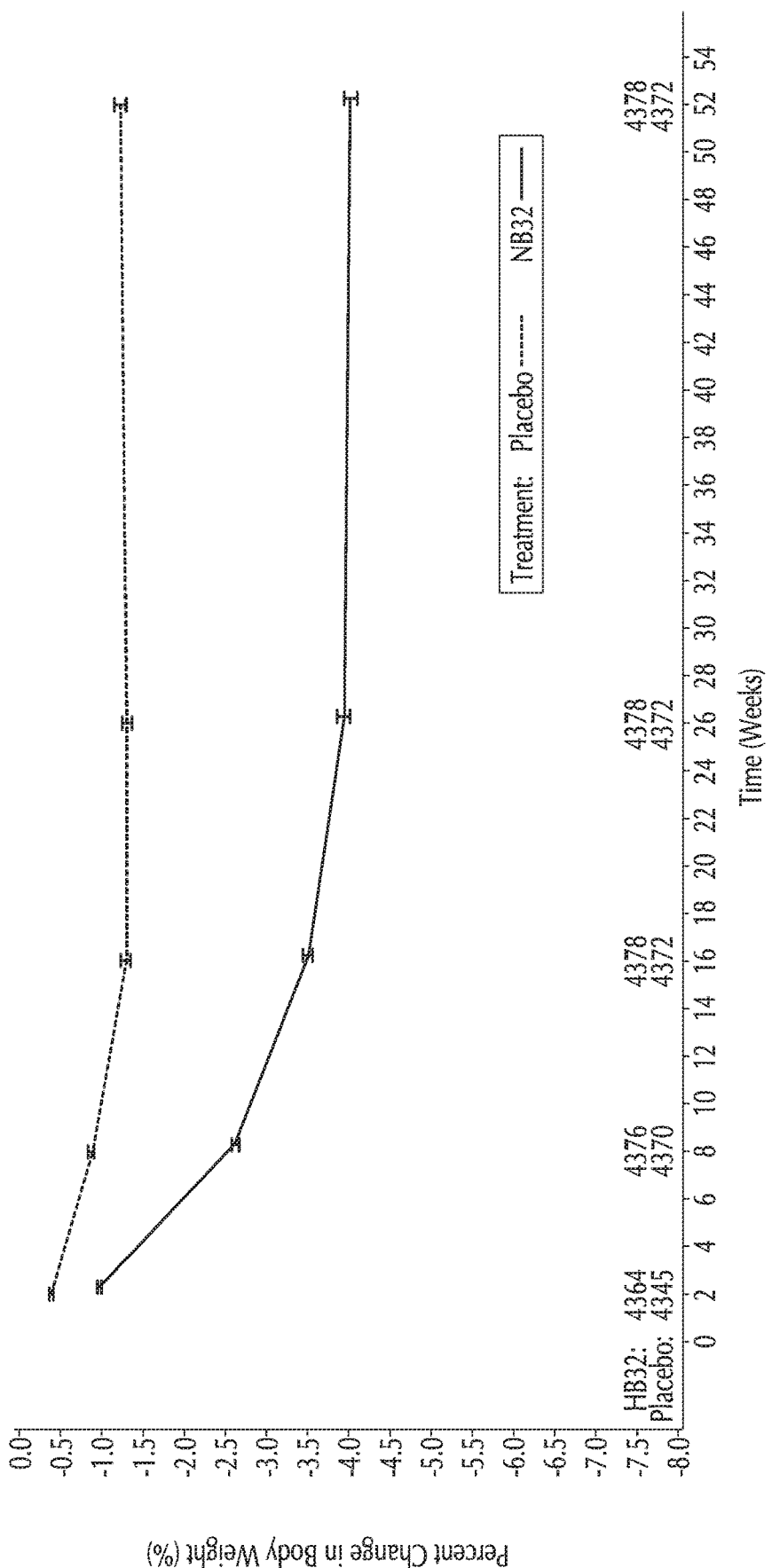

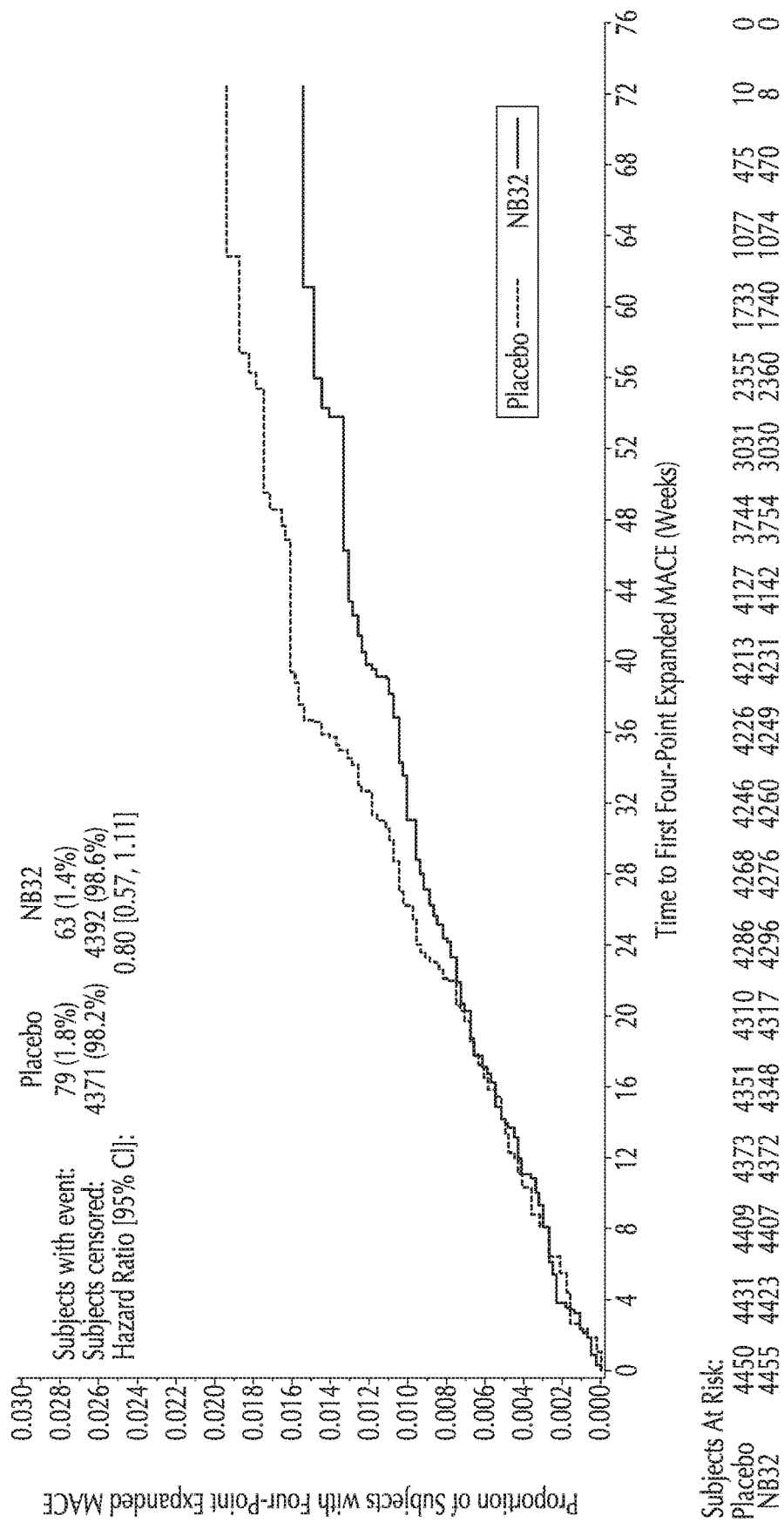

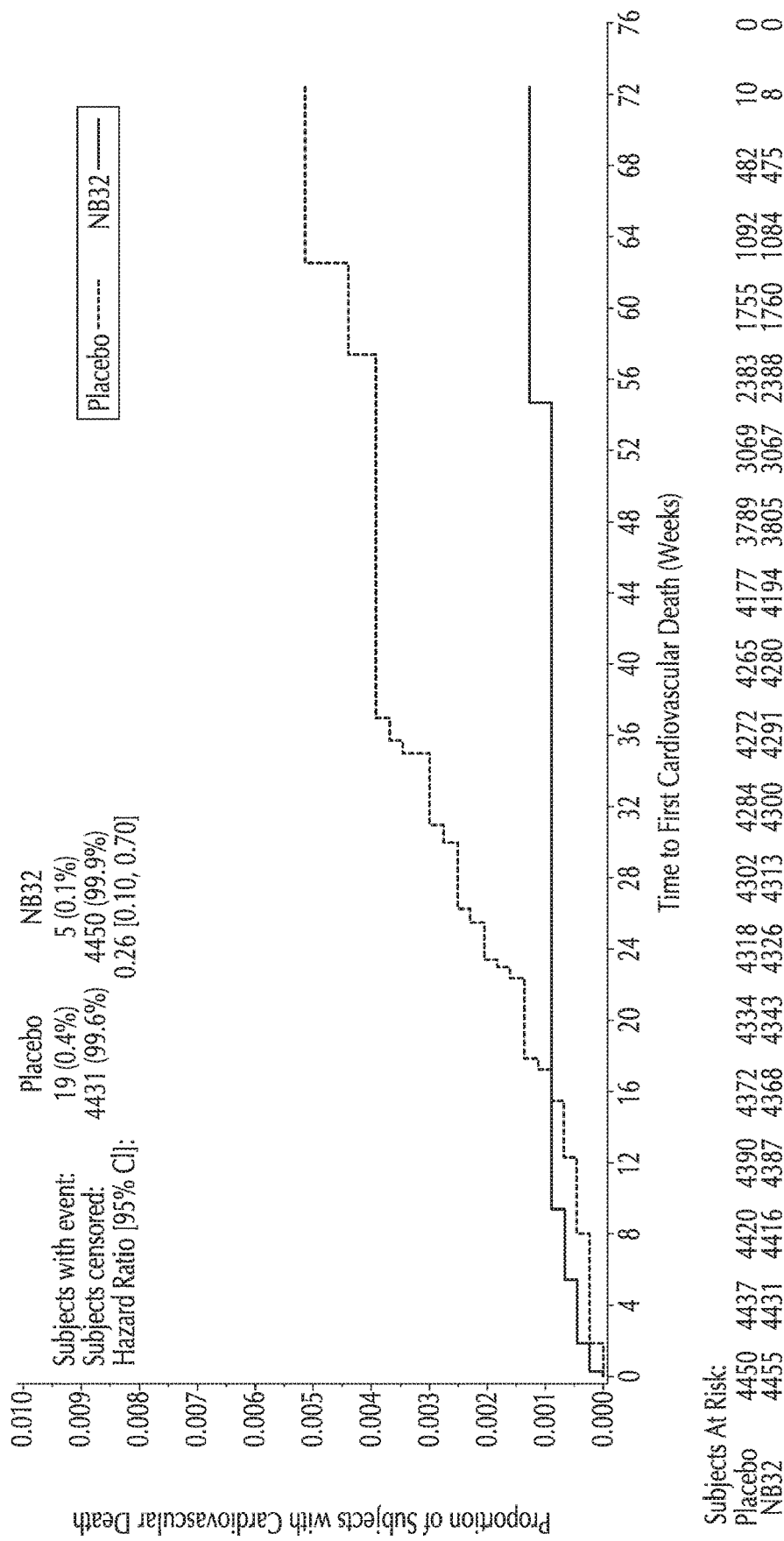

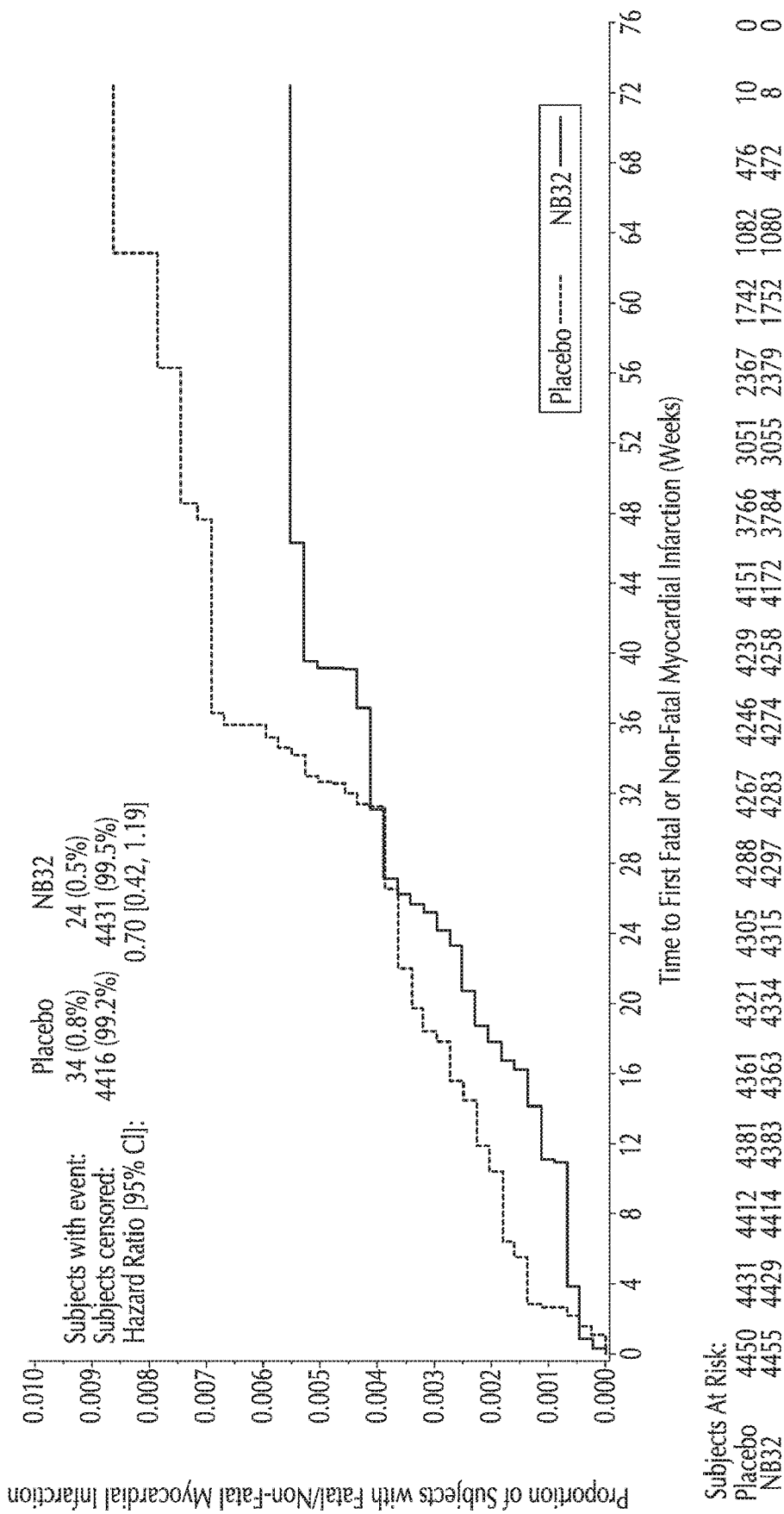

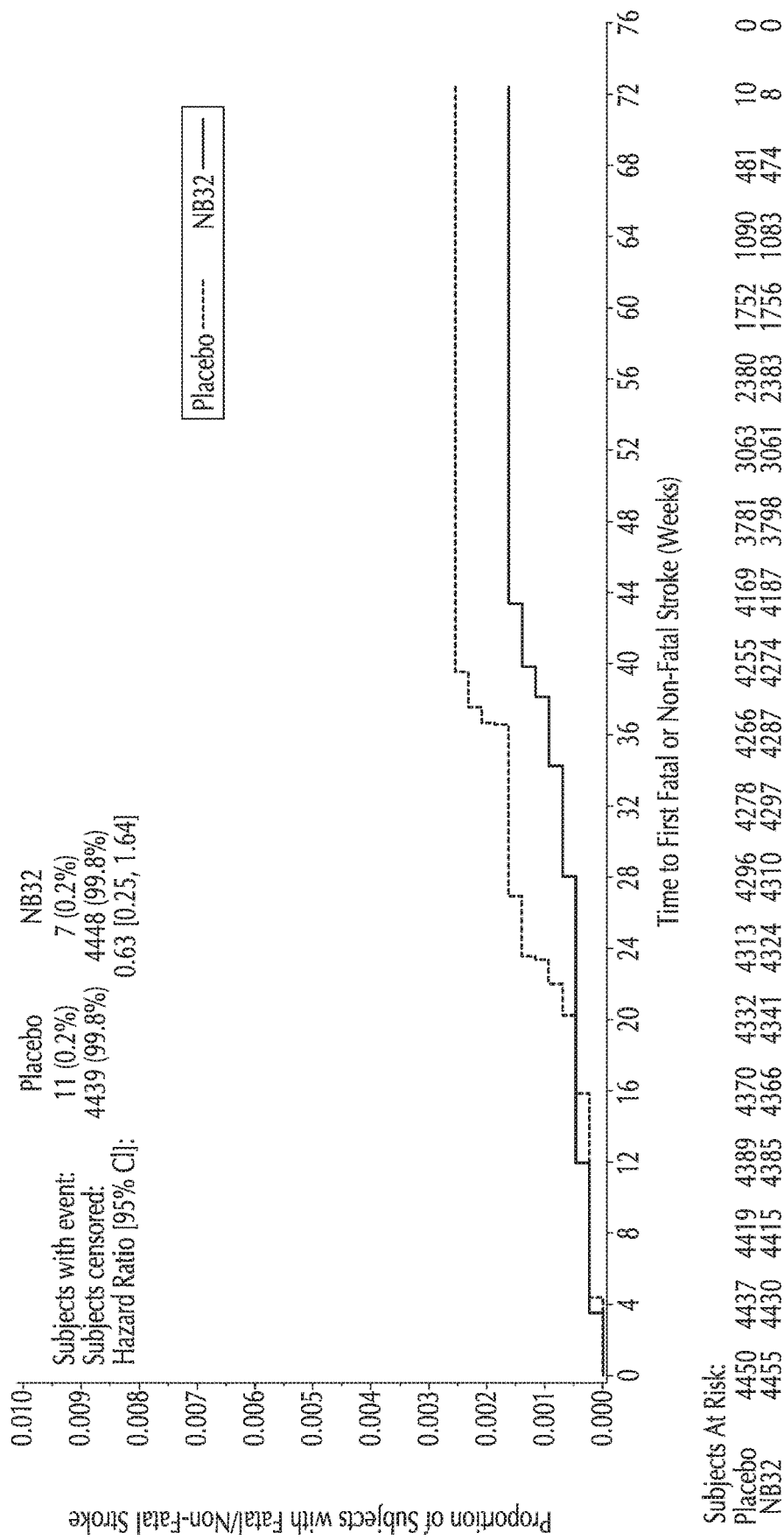

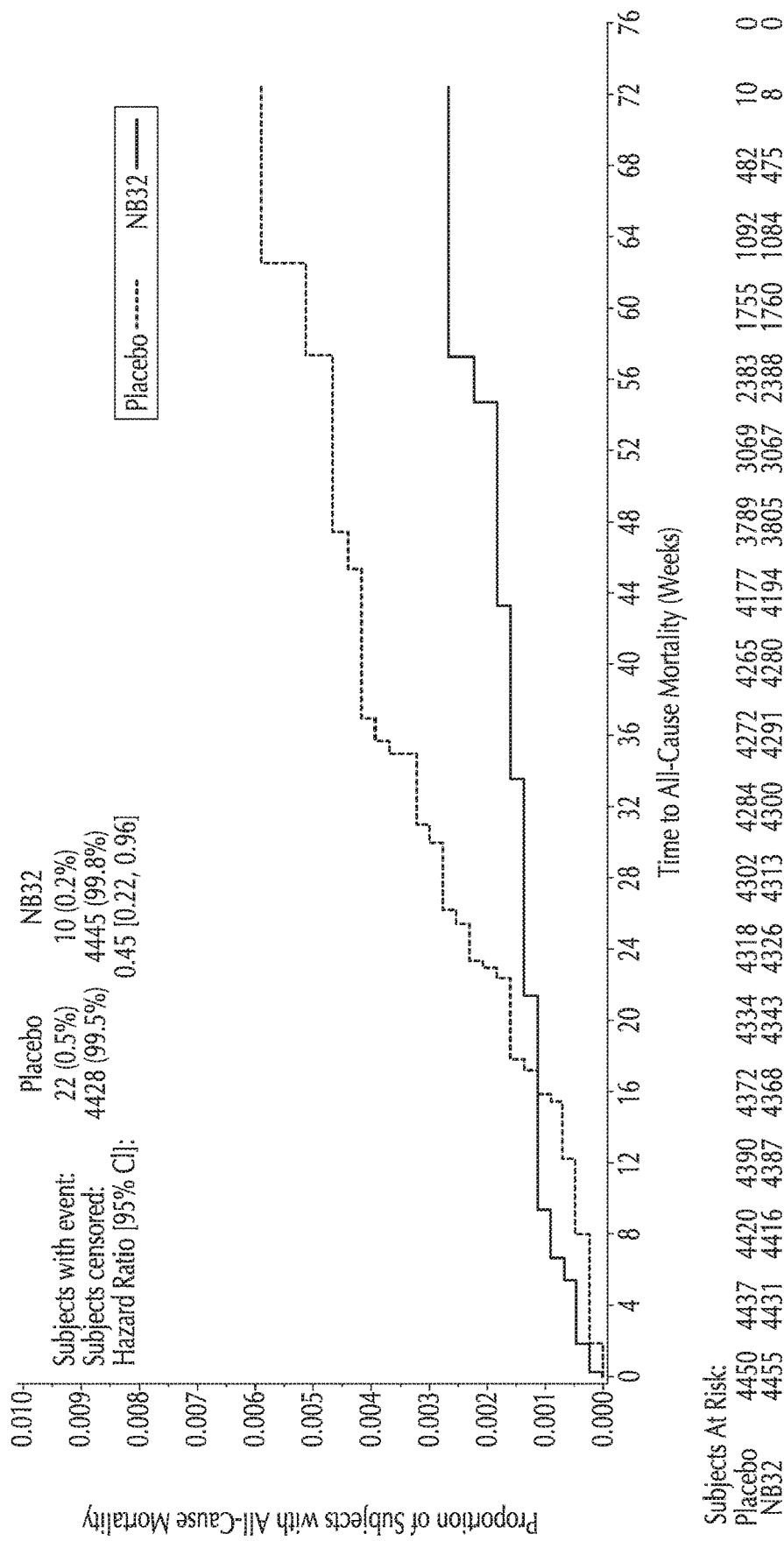

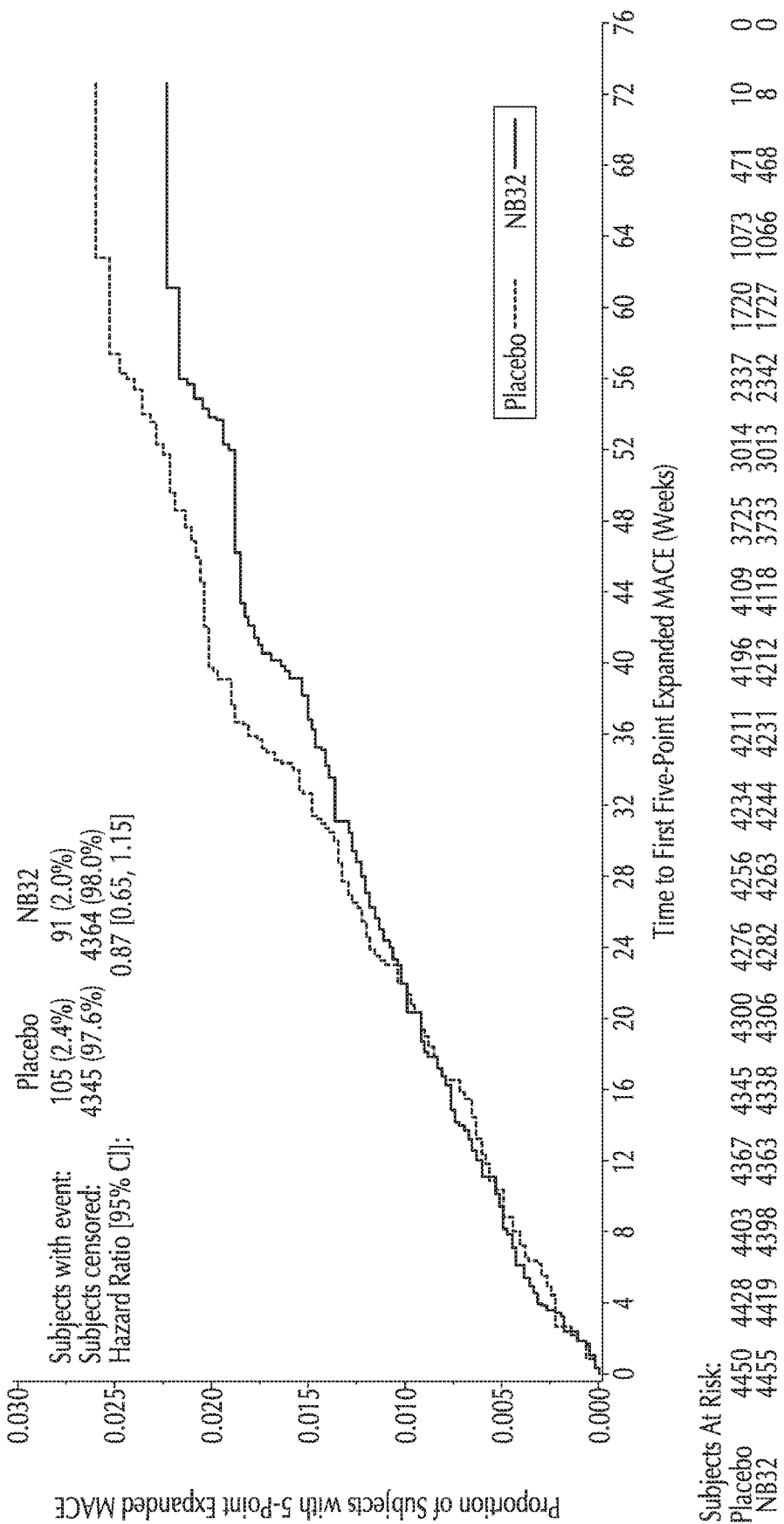

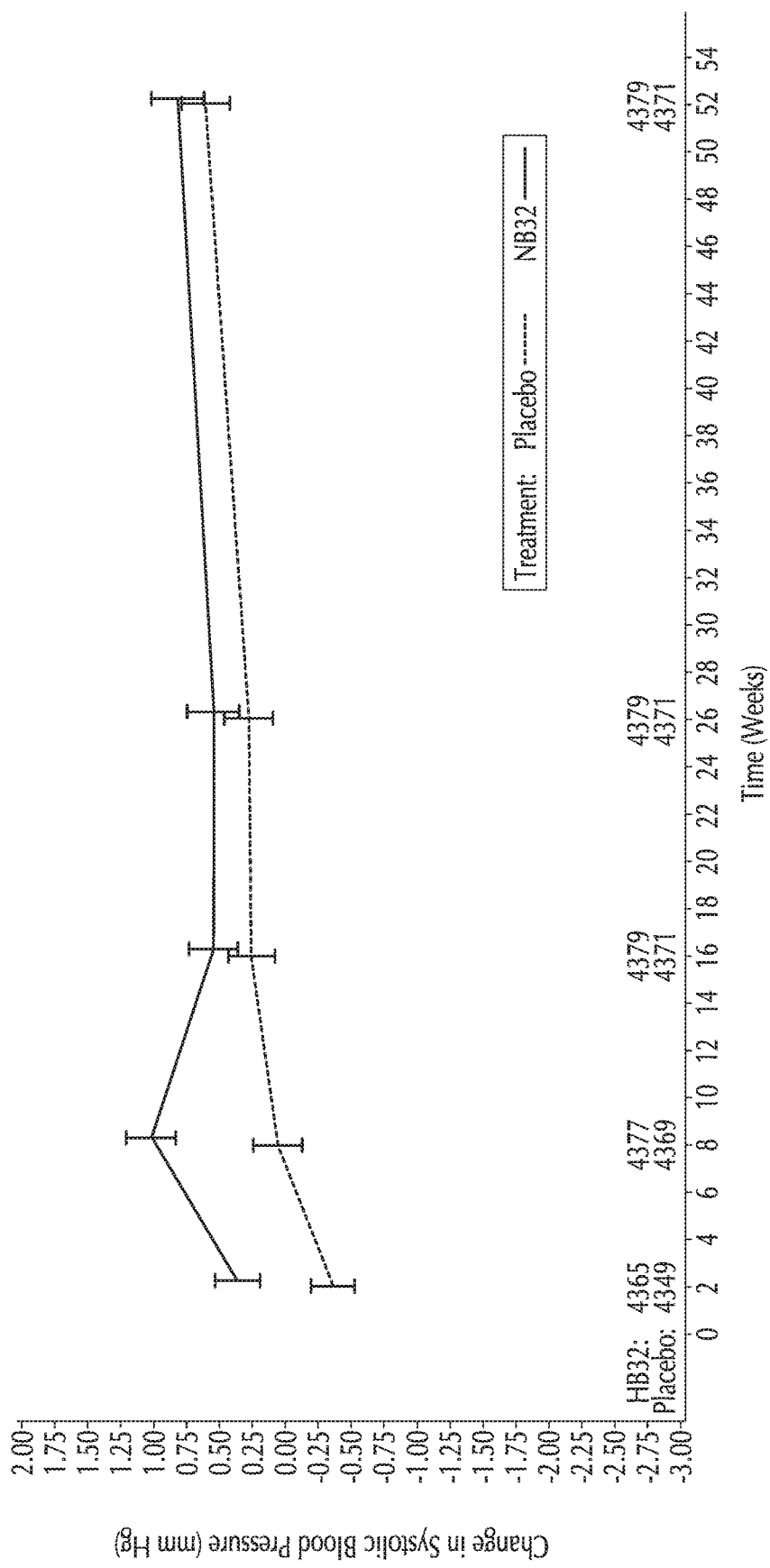

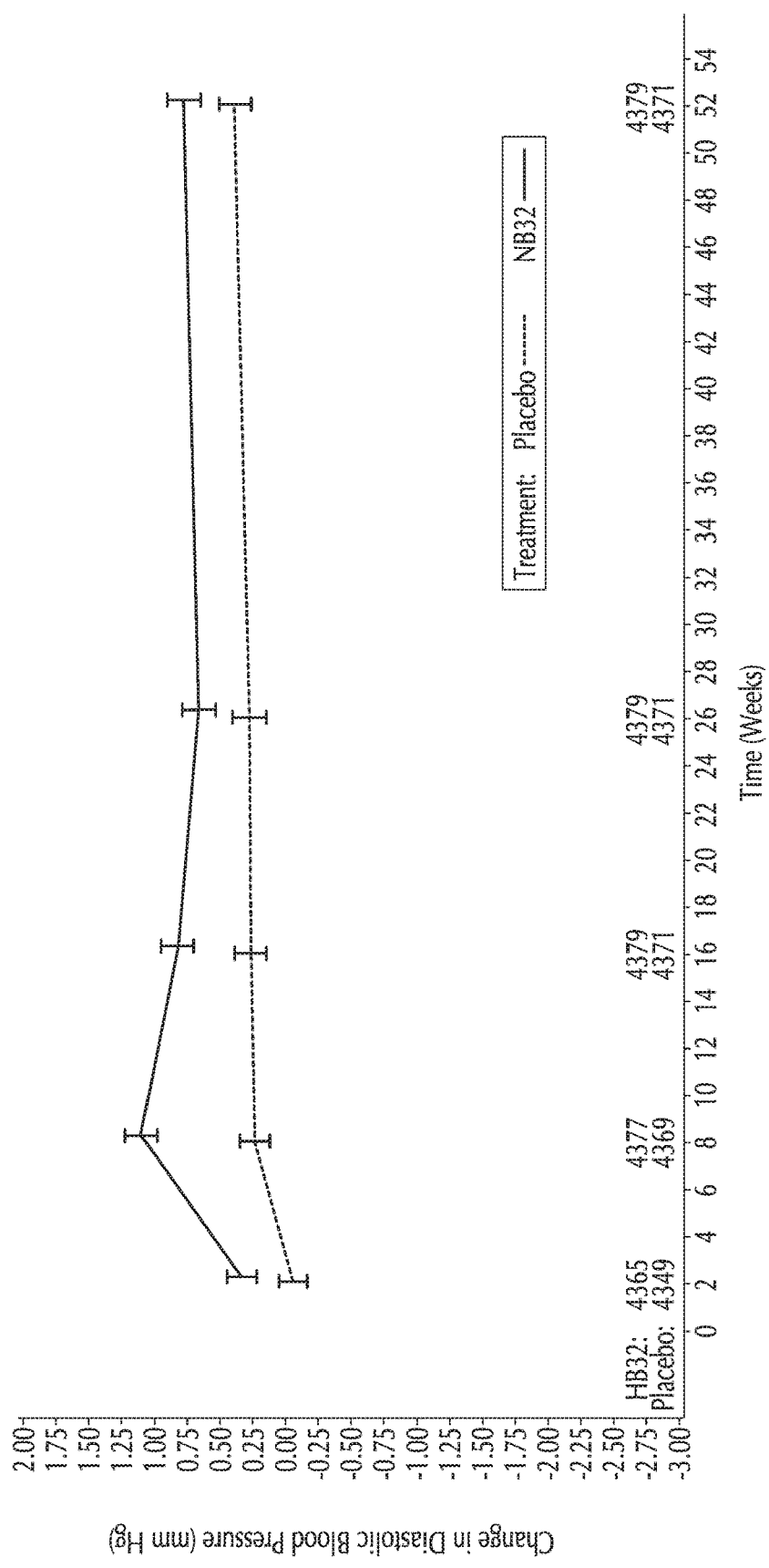

COMPOSITIONS AND METHODS FOR REDUCING MAJOR ADVERSE CARDIOVASCULAR EVENTS

INCORPORATION BY REFERENCE TO RELATED APPLICATIONS

The present application is a continuation of U.S. application Ser. No. 15/101,878, which is the U.S. National Stage Entry of PCT/US14/68527, filed Dec. 4, 2014, which claims the benefit of priorities to U.S. Appl. Nos. 61/913,216, filed Dec. 6, 2013; 61/914,938, filed Dec. 11, 2013; 61/984,580, filed Apr. 25, 2014, and Ser. No. 14/322,810, filed Jul. 2, 2014, issued as U.S. Pat. No. 8,969,371 each of which is hereby incorporated by references in its entirety.

BACKGROUND

Cardiovascular disease ("CVD"), which includes heart disease, is a class of diseases that involve the heart, the blood vessels (arteries, capillaries, and veins) or both. Cardiovascular disease refers to any disease that affects the cardiovascular system, principally cardiac disease, vascular diseases of the brain and kidney, and peripheral arterial disease. The causes of cardiovascular disease are diverse but atherosclerosis and/or hypertension are the most common.

Cardiovascular disease is the number one cause of death worldwide. Accordingly to WHO March 2013 Fact Sheet N 317, an estimated 17.3 million people died from CVDs in 2008, representing 30% of all global deaths. Of these deaths, an estimated 7.3 million were due to coronary heart disease and 6.2 million were due to stroke. The number of people who die from CVDs, mainly from heart disease and stroke, will increase to reach 23.3, million by 2030. CVDs are projected to remain the single leading cause of death. Therefore, there exists a need to develop new CVD treatments.

Major Adverse Cardiovascular Events ("MACEs") include three primary measurements: nonfatal myocardial infarction ("MI"), nonfatal stroke, and cardiovascular death. These major adverse cardiovascular events represent serious ischemic events and are widely used endpoints in cardiovascular outcome trials.

In view of the foregoing, there is a need to develop effective treatments to reduce the risk of MACE in patients at an increased risk of MACE.

Obesity has been defined in terms of body mass index (BMI). BMI is calculated as weight $(kg)/[height (m)]^2$. According to the guidelines of the U.S. Centers for Disease Control and Prevention (CDC) and the World Health Organization (WHO), for adults over 20 years old, BMI is categorized as follows: below 18.5 is considered underweight, 18.5-24.9 is considered normal, 25.0-29.9 is considered overweight, and 30.0 and above is considered obese (World Health Organization. Physical status: The use and interpretation of anthropometry. Geneva, Switzerland: World Health Organization 1995. WHO Technical Report Series).

In most of the anti-obesity drug clinical studies, people with type 1 or 2 diabetes and other serious medical conditions such as increase risk of major adverse cardiovascular events (MACE) are excluded. As such, there is a need to develop effective anti-obesity treatments in these at risk patient populations.

SUMMARY

Some embodiments disclosed herein relate to compositions, kits, uses, systems and methods for reducing the risk of major adverse cardiovascular events (MACE) comprising naltrexone and bupropion, or pharmaceutically acceptable salts thereof. One embodiment is a method of treating a subject at increased risk of major adverse cardiovascular event (MACE) comprising: identifying a subject at increased risk of MACE; and administering to the subject an amount of naltrexone and bupropion, or a pharmaceutically acceptable salt thereof effective to reduce the increased risk.

One embodiment is a method of treating a subject, comprising: identifying a subject having or at risk of having unstable angina; and reducing the risk of myocardial infarction or the risk of death from a cardiovascular event by administering to the subject an effective amount of naltrexone and bupropion, or a pharmaceutically acceptable salt thereof effective to reduce the increased risk.

One embodiment is a method of treating a subject, comprising: prescribing to a subject a course of treatment including repeated administration of naltrexone and bupropion over a period of at least 10 days; and advising the subject or providing information to the subject that treatment with the compound can reduce the risk of a major adverse cardiovascular event.

One embodiment is a method of treating a subject, comprising: identifying a subject at risk of one or more adverse cardiovascular events; and repeatedly administering to the subject naltrexone and bupropion under a protocol wherein the risk of one or more adverse cardiovascular events is reduced.

One embodiment is a method of treating a subject, comprising identifying a subject not known to have an elevated risk of a major adverse cardiovascular event (MACE) in comparison to other subjects of similar age, race, or gender, but desirous of reducing their risk of MACE; and repeatedly administering to the subject naltrexone and bupropion under a protocol wherein the risk of MACE is reduced.

One embodiment is a method of treating a subject comprising: identifying a subject receiving a standard of care pharmaceutical intervention for at least one of a cardiovascular disease or diabetes, and administering to the subject as an adjunct to the standard of care pharmaceutical intervention an effective amount of naltrexone and bupropion, or pharmaceutically acceptable salts thereof, to lower the risk of MACE in the subject.

One embodiment is a method of treating a subject comprising: identifying a subject receiving a standard of care pharmaceutical intervention for depression, and administering to the subject as an adjunct to the standard of care pharmaceutical intervention an effective amount of naltrexone and bupropion, or pharmaceutically acceptable salts thereof, and an antidepressant to lower the risk of MACE in the subject.

One embodiment is a method of providing a drug, comprising: prescribing to a subject a plurality of individual dosage units of naltrexone and bupropion or pharmaceutically-acceptable salt thereof; and advising the subject that a course of treatment with the compound or salt reduces the risk of major adverse cardiovascular events.

One embodiment is a method of providing a drug, comprising: providing a container to a distributor, pharmacy, care provider, or patient, the container comprising a plurality of individual dosage units of naltrexone and bupropion, or a pharmaceutically acceptable salt thereof; and providing to the distributor, pharmacy, care provider, or patient written information that a course of treatment with the compound or salt thereof can reduce the risk of major adverse cardiovascular events.

One embodiment is a method for marketing a compound, comprising: advising potential prescribers of naltrexone and bupropion or a pharmaceutically-acceptable salt thereof that a course of therapy with the compound or the salt thereof reduces the risk of major adverse cardiovascular events; and supplying unit dosage forms of the compound or the salt thereof for sale to patients to whom the prescribers prescribe the compound or salt thereof.

Some embodiments of the present disclosure relate to methods for preventing or delaying the onset of a major adverse cardiovascular event comprising: selecting for treatment a subject who is not currently at increased risk of MACE; and administering to said subject an amount of naltrexone, or a pharmaceutically acceptable salt thereof and bupropion, or a pharmaceutically acceptable salt thereof.

Some embodiments of the present disclosure relate to methods for treating overweight and obesity using naltrexone and bupropion, or pharmaceutically acceptable salts thereof in a subject is at increased risk of adverse cardiovascular outcomes or increased risk of MACE. In some embodiments, the subject (e.g., patient or patient population) being treated by the methods disclosed herein is overweight or obese and at increased risk of an adverse cardiovascular event. In some embodiments, the subject has one or more of the characteristics at the time of treatment selected from the subpopulations described in Table 8. In some embodiments, the subject has had type 2 diabetes for less than 6 years. In some embodiments, the subject is a current smoker, optionally does not have type 2 diabetes. In some embodiments, the subject is at risk of adverse cardiovascular outcomes but does not have type 2 diabetes. In some embodiments, the subject is over 65 years old. In some embodiments, the subject is a male. In some embodiments, the subject is not a Caucasian. In some embodiments, the subject has a BMI category of ≥35 kg/m² and less than 40 kg/m². In some embodiments, the subject does not have type 2 diabetes or is not on any antidiabetic medications, for example, insulin, metformin, or thiazolidinediones. In some embodiments, the subject has renal impairment characterized by GFR≥90 mL/min. In some embodiments, the subject is currently using one or more beta blocker agents. In some embodiments, the subject is currently using one or more diuretics. In some embodiments, the subject is not using a concomitant medication of one or more angiotensin II receptor blockers (ARB) or angiotensin-converting enzyme inhibitors (ACEI). In some embodiments, the subject is currently using one or more calcium channel blockers. In some embodiments, the subject is currently using one or more medications selected from GLP-1 receptor agonists. DPP-4 inhibitors, or sulfonylurea. In some embodiments, the subject is currently using one or more scrotonin reuptake inhibitors. In some embodiments, the subject does not have depression or is not currently using any anti-depression medications.

In some embodiments, the methods described herein reduce the risk of adverse cardiovascular events. In some embodiments, the methods described herein reduce the risk of MACE. In some embodiments the methods reduce the predicted severity of an adverse cardiovascular event. In some embodiments the methods decrease the predicted mortality from an adverse cardiovascular event. In some embodiments the methods increase the predicted life expectancy of the subject. In some embodiments the methods increase the predicted time period between adverse cardiovascular events. In some embodiments the methods increase the effectiveness of a cardiovascular intervention in the subject. In some embodiments the methods favorably modulate a diagnostic indicator predictive of a major adverse cardiovascular event. In some embodiments the methods decrease the progression of cardiovascular disease.

In some embodiments the subject has Type II diabetes (T2DM). In some embodiments the subject has existing cardiovascular disease. In some embodiments the subject has congestive heart failure. In some embodiments the subject has a family history of cardiovascular disease. In some embodiments the subject is a smoker. In some embodiments the subject is genetically predisposed to cardiovascular disease. In some embodiments the subject has or has had cardiac arrhythmia. In some embodiments the subject has or has had atrial fibrillation, ventricular fibrillation, or tachyarrhythmia. In some embodiments the subject does not have sinus tachycardia. In some embodiments the subject has unstable angina. In some embodiments the subject has hypertension. In some embodiments the subject is overweight. In some embodiments the subject is obese. In some embodiments the subject has had a stroke. In some embodiments the subject has an aneurysm. In some embodiments the subject is at increased risk of stroke. In some embodiments the subject has elevated triglycerides, elevated LDL, and/or low HDL.

In some embodiments the subject is not concurrently taking a statin. In some embodiments the subject is selected for having a characteristic listed in Table 5, 6 and/or 8. In some embodiments the subject is not a current smoker.

In some embodiments the adverse cardiovascular event is cardiovascular death, nonfatal myocardial infarction, cardiac arrhythmia, or nonfatal stroke. In some embodiments the major adverse cardiovascular event is cardiovascular death. In some embodiments the cardiovascular death comprises death resulted from fatal myocardial infarction and stroke. In some embodiments the major adverse cardiovascular event is non-fatal stroke. In some embodiments the major adverse cardiovascular event is non-fatal myocardial infarction. In some embodiments the major adverse cardiovascular event comprises both fatal and non-fatal stroke. In some embodiments the major adverse cardiovascular event comprises cardiac arrhythmia. In some embodiments the major adverse cardiovascular event comprises both fatal and non-fatal myocardial infarction. In some embodiments the major adverse cardiovascular event further comprises progression from unstable angina to myocardial infarction or death.

In some embodiments one or both of naltrexone and bupropion, or a pharmaceutically acceptable salt thereof is administered in a sustained release formulation.

In some embodiments, the subject is treated for at least 12 weeks. In some embodiments, the subject is treated for at least 20 weeks. In some embodiments the subject is treated for at least 26 weeks. In some embodiments the subject is treated for at least 52 weeks. In some embodiments the subject is treated for at least 78 weeks. In some embodiments the subject is treated for at least 104 weeks.

In some embodiments the subject's vital signs do not change by more than 10%, or 5% during the course of treatment. In some embodiments the vital sign is selected from the group of blood pressure, systolic blood pressure, diastolic blood pressure, and/or heart rate.

Some embodiments provided herein include methods in which the subject is being treated according to the standard of care with existing medications, including medications to treat diabetes, dyslipidemia, and hypertension. Thus, the embodiments provided herein include administering Naltrexone SR/Bupropion SR to a subject that is at risk of MACE and that is being treated according to the standard of care with a diabetes, dyslipidemia, or hypertension medication. The embodiments provided herein also include administering Naltrexone SR/Bupropion SR to a subject that is taking a diabetes, dyslipidemia, or hypertension medication. In some embodiments the subject is concurrently taking a medication for management of one or more of a cardiovascular condition or diabetes. In some embodiments the subject is concurrently taking one or more medications for management of one or more of hypertension, dyslipidemia or a blood glucose condition. In some embodiments the subject is concurrently taking a medication for management of depression. In some embodiments the subject is administered a naltrexone and bupropion, or pharmaceutically acceptable salts thereof, and one or more additional pharmaceutical compounds, wherein the combination is selected from a combination listed in Tables 1-3. In some embodiments the methods further comprise coadministering an effective amount of an antidepressant compound. In some embodiments the antidepressant compound has been approved for antidepressant use by a governmental agency that determines the safety and efficacy of drugs. In some embodiments the methods further comprise coadministering an effective amount of an antidepressant compound selected from a selective serotonin reuptake inhibitor, a serotonin-norepinephrine reuptake inhibitor, a serotonin antagonist and reuptake inhibitor, a TAARI agonist, a tricyclic antidepressant, a tetracyclic antidepressant, or a monoamine oxidase inhibitor. In some embodiments the methods further comprise coadministering an effective amount of a selective serotonin reuptake inhibitor.

In some embodiments subject identification is done independent of one or more of the following patient characteristics: weight; waist circumference; gender; age under 45 years; blood pressure; a history of documented myocardial infarction >3 months prior to the identifying; a history of coronary revascularization; a history of carotid or peripheral revascularization; angina with ischemic changes; ECG changes on a graded exercise test; positive cardiac imaging study; ankle brachial index <0.9 within 2 years prior to the identifying; or, >50% stenosis of a coronary artery, carotid artery, or lower extremity artery within 2 years prior to the identifying.

In some embodiments the subject is non-obese. In some embodiments the subject is non-overweight. In some embodiments the subject is not part of a weight management program during the treatment. In some embodiments the subject's weight is not monitored during the course of administration. In some embodiments the subject is participating in a weight management program during the treatment. In some embodiments the subject's weight is monitored during the course of administration.

In some embodiments the subject is between 18 to 44 years old. In some embodiments the subject is greater than 44 years old. In some embodiments the subject is not an 18 to 49 year-old female. In some embodiments the subject is an 18 to 49 year-old female. In some embodiments the subject has a body mass index of <27 kg/m$^3$. In some embodiments the subject has a body mass index of at least 27 kg/m$^2$. In some embodiments the subject is a female with a waist circumference <88 cm. In some embodiments the subject is a female with a waist circumference of at least 88 cm. In some embodiments the subject is a male with a waist circumference <102 cm. In some embodiments the subject is a male with a waist circumference of at least 102 cm.

In some embodiments the subject has type 2 diabetes or a confirmed diagnosis of cardiovascular disease. In some embodiments the subject does not have type 2 diabetes or a confirmed diagnosis of cardiovascular disease. In some embodiments the subject has either a confirmed diagnosis of cardiovascular disease or a high likelihood of cardiovascular disease, and wherein the subject has at least one of: a history of documented myocardial infarction >3 months prior to the identifying; a history of coronary revascularization; a history of carotid or peripheral revascularization; angina with ischemic changes; ECG changes on a graded exercise test; positive cardiac imaging study; ankle brachial index <0.9 within 2 years prior to the identifying; or >50% stenosis of a coronary artery, carotid artery, or lower extremity artery within 2 years prior to treatment. In some embodiments the subject has either a confirmed diagnosis of cardiovascular disease or a high likelihood of cardiovascular disease, and wherein the subject does not have at least one of: a history of documented myocardial infarction >3 months prior to the identifying; a history of coronary revascularization; a history of carotid or peripheral revascularization; angina with ischemic changes; ECG changes on a graded exercise test; positive cardiac imaging study; ankle brachial index <0.9 within 2 years prior to the identifying; or >50% stenosis of a coronary artery, carotid artery, or lower extremity artery within 2 years prior to treatment. In some embodiments the subject has type 2 diabetes and no more than one of: hypertension at >145/95 mm Hg, dyslipidemia requiring pharmacotherapy, documented low HDL within 12 months prior, or is a current tobacco user.

In some embodiments the subject has a history of atrial fibrillation. In some embodiments the subject has had a myocardial infarction within 3 months prior treatment with the methods. In some embodiments the subject has a history of angina pectoris Grade 1 or Grade IV as per the Canadian Cardiovascular Society grading scheme. In some embodiments the subject has a history of cerebrovascular disease. In some embodiments the subject has a history of stroke. In some embodiments the subject has a history of tachycardia other than sinus tachycardia. In some embodiments the subject has a history of sinus tachycardia. In some embodiments the subject has a planned bariatric surgery, cardiac surgery, or coronary angioplasty.

In some embodiments the subject does not have a history of seizures, cranial trauma, or a condition that predisposes the subject to seizures. In some embodiments the subject has a history of seizures, cranial trauma, or a condition that predisposes the subject to seizures. In some embodiments the subject has a history of mania, current diagnosis of active psychosis, current diagnosis of active bulimia, or current diagnosis of anorexia nervosa. In some embodiments the subject does not have a history of mania, current diagnosis of active psychosis, current diagnosis of active bulimia, or current diagnosis of anorexia nervosa.

In some embodiments the subject has a life expectancy of less than 4 years. In some embodiments the subject has a life expectancy of at least 4 years.

In some embodiments both naltrexone and bupropion, or pharmaceutically acceptable salts thereof, are in sustained release form. In some embodiments the subject is not instructed to discontinue the naltrexone and bupropion if blood pressure increases by a value, wherein the value is 10 mmHg or more. In some embodiments the naltrexone and bupropion is administered one, two, three, or four times a day. In some embodiments the naltrexone or pharmaceutically acceptable salt thereof, is administered in a daily dosage of 4-50 mg. In some embodiments the bupropion or pharmaceutically acceptable salt thereof, is administered in a daily dosage of 50-400 mg.

In some embodiments the methods reduce at least one of: the risk of one or more major adverse cardiovascular events (MACE) in a subject; the predicted severity of an adverse cardiovascular event; the predicted mortality from an adverse cardiovascular event, and combinations thereof, wherein the reduction in risk, predicted severity or predicted mortality is a reduction of at least or at least about 5%, 10%, 15%, 20%, 25%, 30%, 35%, 40%, 45%, 50%, 60%, 70%, 80%, or 90% relative to a subject at the same level of risk of MACE, predicted severity of an adverse cardiovascular event or predicted mortality from an adverse cardiovascular event, but who is not receiving treatment by administration of naltrexone and bupropion.

In some embodiments the methods are effective to decrease the progression of cardiovascular disease in a subject, and wherein the decrease in the progression of cardiovascular disease is a decrease of at least or at least about 5%, 10%, 15%, 20%, 25%, 30%, 35%, 40%, 45%, 50%, 60%, 70%, 80%, or 90% in the progression of cardiovascular disease, relative to a subject at the same level of cardiovascular disease progression, but who is not receiving treatment by administration of naltrexone and bupropion.

In some embodiments the methods are effective to increase the predicted life expectancy of the subject, or to increase the predicted time period until next occurrence of an adverse cardiovascular event, and wherein the increase is at least or at least about 1 month, 2 months, 3 months, 4 months, 5 months, 6 months, 7 months, 8 months, 9 months, 10 months, 11 months, 12 months, 14 months, 16 months, 18 months, 20 months, or 24 months, relative to a subject at the same level of risk of MACE, but who is not receiving treatment by administration of naltrexone and bupropion.

In some embodiments the methods increase the effectiveness of a cardiovascular intervention in a subject, wherein the increase is at least or at least about at least or at least about 5%, 10%, 15%, 20%, 25%, 30%, 35%, 40%, 45%, 50%, 60%, 70%, 80%, or 90%, relative to the expected effectiveness of a cardiovascular intervention in a subject at the same level of risk of MACE receiving the same cardiovascular intervention, but who is not receiving treatment by administration of naltrexone and bupropion.

In some embodiments the methods favorably modulate a diagnostic indicator predictive of a major adverse cardiovascular event, wherein the favorable modulation is of at least or at least about at least or at least about 5%, 10%, 15%, 20%, 25%, 30%, 35%, 40%, 45%, 50%, 60%, 70%, 80% or 90%, relative to the diagnostic indicator predictive of a major adverse cardiovascular event in a subject at the same level of risk of MACE, but who is not receiving treatment by administration of naltrexone and bupropion.

In some embodiments the reduction in risk or improvement in outcome is achieved in less than 16 weeks of treatment, after 16 weeks of treatment, in less than 20 weeks of treatment, in less than 24 weeks of treatment, in less than 28 weeks of treatment, or in less than 52 weeks of treatment.

In some embodiments the subject does not lose more than 5%, 4%, 3%, 2%, 1% of their body weight. In some embodiments the reduction in risk of MACE or improvement in outcome is achieved and the subject has not lost more than 5%, 4%, 3%, 2%, 1% of their body weight.

In some embodiments the subject's blood pressure does not change by more than 5%, 4%, 3%, 2%, 1% or 0.5%. In some embodiments the subject's blood pressure increases by 0.5%, 1%, 2%, 3%, 4% or 5%. In some embodiments the blood pressure is systolic blood pressure, diastolic blood pressure, or both. In some embodiments the blood pressure is measured after 2, 8, 16, 20, 24, 26, 28, 30 or 52 weeks of treatment. In some embodiments the change in blood pressure is measured relative to a pretreatment baseline.

In some embodiments the methods may increase the time until first incidence of one or more events selected from the group consisting of: MACE, Four-point Expanded MACE, Five-point Expanded MACE, CV death, nonfatal MI, stroke, fatal stroke, nonfatal stroke. Nonfatal HUSA (hospitalization due to unstable angina), coronary revascularization procedure, and/or all-cause mortality.

In some embodiments the adverse outcome is one or more events selected from the group consisting of: MACE, Four-point Expanded MACE, Five-point Expanded MACE, CV death, nonfatal MI stroke, fatal stroke, nonfatal stroke. Nonfatal HUSA (hospitalization due to unstable angina), coronary revascularization procedure, and/or all-cause mortality.

One embodiment is naltrexone and bupropion for use in any of the preceding methods. One embodiment is use of naltrexone and bupropion for reducing the risk of a major adverse cardiovascular event. One embodiment is use of naltrexone and bupropion for the preparation of a medicament for reducing the risk of a major adverse cardiovascular event. One embodiment is use of naltrexone and bupropion for the preparation of a medicament for reducing the risk of a major adverse cardiovascular event, wherein the compound is for use in accordance with a method set forth in any one of the preceding claims. In some embodiments, the naltrexone and/or bupropion, or pharmaceutically acceptable salts thereof, is in sustained release or extended release form.

BRIEF DESCRIPTION OF THE DRAWINGS

FIG. 1 is a graphic depiction of the study design of Examples 1 and 2.

FIG. 2 illustrates the time to first major adverse cardiovascular event (MACE) for patients receiving naltrexone and bupropion (NB32) or placebo in an embodiment.

FIG. 3 illustrates the percent change in body weight from baseline over time for patients receiving naltrexone and bupropion (NB32) and placebo in an embodiment.

FIG. 4 illustrates the time to first four-point expanded major adverse cardiovascular event (MACE) for patients receiving naltrexone and bupropion (NB32) or placebo in an embodiment.

FIG. 5 illustrates the time to cardiovascular death for patients receiving naltrexone and bupropion (NB32) or placebo in an embodiment.

FIG. 6 illustrates the time to first myocardial infarction for patients receiving naltrexone and bupropion (NB32) or placebo in an embodiment.

FIG. 7 illustrates the time to first stroke for patients receiving naltrexone and bupropion (NB32) or placebo in an embodiment.

FIG. 8 illustrates the time to all-cause mortality for patients receiving naltrexone and bupropion (NB32) or placebo in an embodiment.

FIG. 9 illustrates the time to first five-point expanded major adverse cardiovascular event (MACE) for patients receiving naltrexone and bupropion (NB32) or placebo in an embodiment.

FIG. 10 illustrates the mean change in systolic blood pressure from baseline over time for patients receiving naltrexone and bupropion (NB32) or placebo in an embodiment.

FIG. 11 illustrates the mean change in diastolic blood pressure from baseline over time for patients receiving naltrexone and bupropion (NB32) or placebo in an embodiment.

DETAILED DESCRIPTION

The combination of naltrexone SR and bupropion SR (Contrave®, or NB) is being developed by Orexigen Therapeutics, Inc, for weight loss and maintenance of weight loss in overweight and obese individuals. To explore the risk of MACE in overweight and obese subjects treated with naltrexone and bupropion, a double-blind, randomized, placebo-controlled study designed to rule out excess cardiovascular (CV) risk in overweight and obese subjects at increased risk of adverse CV outcomes was conducted. This study, described in Example 1, was required by the FDA prior to approval of Contrave because the active ingredients in Contrave, particularly bupropion, were known to increase blood pressure. The FDA was concerned that an increase in blood pressure, while acceptable for the general population, would lead to an unacceptable increase in adverse cardiovascular outcomes in an overweight/obese patient population. Therefore, patients at higher risk of MACE were treated with Contrave or placebo to determine if Contrave led to an unacceptable increase in adverse cardiovascular outcomes.

Example 2 below summarizes some results of this clinical study, which demonstrates that treatment with Naltrexone SR/Bupropion SR decreases the occurrence of MACE in overweight and obese subjects with cardiovascular risk factors. Briefly stated, fewer subjects in the Naltrexone SR/Bupropion SR treatment group experienced a MACE event compared to placebo.

For example, favorable results were observed in an overweight/obese patient population at risk of MACE that had cardiac arrhythmia and an overweight/obese patient population at risk of MACE that were characterized as having depression, where some such subjects were receiving antidepressant medication, e.g., selective serine reuptake inhibitors (SSRIs), according to the standard of care for treating depression. Favorable results also were observed in an overweight/obese patient population at risk of MACE that was well-treated according to standard of care with existing medications, some of which are known to lower risk of MACE, including medications to treat diabetes, dyslipidemia, and hypertension.

Subjects

The term "subject" refers to an individual, preferably a human, having a medical condition or receiving or being a candidate for receiving medical treatment. With human subjects, the term is often used synonymously with the term "patient." In some embodiments, the subject being treated by the methods disclosed herein is overweight or obese and at increased risk of a major adverse cardiovascular event (MACE). In some embodiments. MACE is cardiovascular death, nonfatal myocardial infarction, nonfatal stroke. In some embodiments, the overweight or obese subject at increased risk of MACE has one or more characteristics or suffers from one or more of: a history of cardiovascular disease (CVD); a current confirmed diagnosis or at high likelihood of CVD; Type 1 diabetes; Type 2 diabetes; dyslipidemia, for example, elevated triglycerides, elevated LDL, or low HDL; hypertension; past or current smoker; a family history of CVD; a genetic predisposition of CVD; unstable angina; cardiac arrhythmia; atrial fibrillation; congestive heart failure; and stroke.

In some embodiments, the subject at increased risk of MACE has a BMI≥27 kg/m$^2$ and ≤50 kg/m$^2$. In some embodiments, the subject at increased risk of MACE is a male at least 50 years in age and having a waist circumference≥102 cm. In some embodiments, the subject at increased risk of MACE is a female at least 45 years in age and having a waist circumference≥88 cm.

In some embodiments, the overweight or obese subjects that are at increased risk of adverse cardiovascular (CV) event or MACE include subjects having one or more of the following conditions:

(a) cardiovascular disease (CVD) (confirmed diagnosis or at an increased risk of CVD) optionally with at least one of the following: a history of documented myocardial infarction >3 months prior to screening or identification; a history of coronary revascularization (e.g., coronary artery bypass graft surgery, stent placement, percutaneous transluminal coronary angioplasty, or laser atherectomy); history of carotid or peripheral revascularization (e.g., carotid endarterectomy, lower extremity atherosclerotic disease atherectomy, repair of abdominal aorta aneurysm, femoral or popliteal bypass); angina with ischemic changes (resting ECG), ECG changes on a graded exercise test (GXT), or positive cardiac imaging study; ankle brachial index <0.9 (by simple palpation) within prior 2 years; and ≥50% stenosis of a coronary, carotid, or lower extremity artery within prior 2 years; and/or (b) Type 2 diabetes mellitus (T2DM), optionally with at least two of the following: hypertension (controlled with or without pharmacotherapy at <145/95 mm Hg); dyslipidemia requiring pharmacotherapy; documented low HDL cholesterol (<50 mg/dL in women or <40 mg/dL in men) within prior 12 months: and current tobacco smoker.

In some embodiments, the subject being treated does not have (i.e., lacks) one or more or all of the following characteristics: (a) a myocardial infarction within 3 months prior to treatment; (b) a history of angina pectoris Grade III or Grade IV as per the Canadian Cardiovascular Society grading scheme; (c) a history of cerebrovascular disease; (d) a history of stroke; (e) a history of tachycardia other than sinus tachycardia; (f) a planned bariatric surgery, cardiac surgery, or coronary angioplasty; (g) a history of seizures, cranial trauma, or a condition that predisposes the subject to seizures; (h) a history of mania, current diagnosis of active psychosis, current diagnosis of active bulimia, or current diagnosis of anorexia nervosa; or (i) a condition with life expectancy less than 4 years.

In some embodiments, a subject increased risk of an adverse cardiovascular outcome is characterized as a subject for whom the likelihood of an adverse cardiovascular outcome, in some embodiments specifically MACE, is at least, or at least about, 10%, 15%, 20%, 25%, 30%, 35%, 40%, 45%, 50%, 55%, 60%, 65%, 70%, 75%, 80%, 85%, 90%, 95%, or 100%, greater than the likelihood of an adverse cardiovascular outcome, or MACE, in the overall population, or an age and/or sex matched population.

In some embodiments, the subject has cardiac arrhythmia. For example the subject can have increased risk of MACE and have cardiac arrhythmia. In some embodiments, the arrhythmia is atrial fibrillation, ventricular fibrillation, or tachyarrhythmia. In some embodiments, the arrhythmia is not sinus tachycardia. In some embodiments, the subject is characterized as having depression. In some embodiments the depression is chronic and not acute or of recent onset. For example the subject can be characterized as having depression and have increased risk of MACE. In some embodiments, the depressed subject is receiving an antidepressant, for example a selective serine reuptake inhibitor (SSRI), according to the standard of care for treating depression. In some embodiments, the subject is being treated according to the standard of care with existing medications, some of which are known to lower risk of MACE, including medications to treat diabetes, dyslipidemia, and hypertension. For example the subject can have increased risk of MACE and be receiving a standard of care medication to treat diabetes, dyslipidemia, or hypertension.

In some embodiments the subject or patient population is selected for having a characteristic listed in Table 5, 6 and/or 8. In some such embodiments, the subject has one or more of the characteristics at the time of treatment selected from the subpopulations described in Table 8, in a preferred in embodiment the point estimate the hazard ratio for subpopulation is selected from less than about 0.85, less than about 0.8, less than about 0.75, less than about 0.70, or less than about 0.65; more preferably the hazard ratio is selected from less than about 0.60, less than about 0.55, less than about 0.50, less than about 0.45, less than about 0.40, less than about 0.35, less than about 0.30, less than 0.25, less than 0.20, less than 0.15, or less than 0.10. In some embodiments, the subject or patient population has one or more of the following characteristics: suffering from CV disease; suffering from CV disease without T2DM; suffering from CV disease with T2DM; suffering from T2DM; suffering from T2DM without CV disease; current smoker; current non-smoker; suffering from hypertension; suffering from dyslipidemia; not suffering from hypertension; not suffering from dyslipidemia; BMI<35 kg/m$^2$; BMI≥35 kg/m$^2$ and <40 kg/m$^2$; BMI≥40 kg/m$^2$; currently taking one or more medications selected from an antihypertensive (including but not limited to: beta blocking agent, diuretic, ACEI/ARB, calcium channel blocker); a lipid altering medication (including but not limited to statins, non-statins); an antidiabetic medication (including but not limited to insulin, thiazolidinediones, metformin, GLP-1/DDP-IV, sulfonylurea); an antidepressant medication (including but not limited to SSRI, non-SSRI); duration of T2DM<6 years; duration of T2DM≥6 years. In some embodiments the subject or patient population is not currently taking statins. In some embodiments the subject or patient population is a current smoker. In some embodiments the subject or patient population has a duration of T2DM<6 years. In some embodiments the subject or patient population has a BMI<40 kg/m$^2$.

In some such embodiments, the subject is a current smoker, optionally does not have type 2 diabetes. In some such embodiments, the subject has had type 2 diabetes for less than 6 years. In some such embodiments, the subject is currently using one or more medications selected from GLP-1 receptor agonists or DPP-4 inhibitors. In some such embodiments, the subject has a BMI category of ≥35 kg/m$^2$ and less than 40 kg/m$^2$. In some such embodiments, the subject is not on any antidiabetic medications. In some such embodiments, the subject is a male. In some such embodiments, the subject is not using metformin. In some such embodiments, the subject is over 65 years old. In some embodiments, the above characteristics are in addition to the subject of patient population being overweight or obese, and preferably at an increased risk of an adverse cardiovascular event, or at increased risk of MACE.

In some embodiments, the subject with one or more of the following characteristics are excluded: currently not taking any lipid altering medication, currently taking metformin, having HbA1c category of less than 7%, has had diabetes for 6 or more years at the time of treatment and having a BMI>40 kg/m$^2$.

Methods

The embodiments provided herein include methods of decreasing the predicted likelihood of an adverse cardiovascular event in a subject, where the methods include administering to a subject (or a population of subjects) an amount of naltrexone and bupropion, or a pharmaceutically acceptable salt thereof effective to decrease the predicted likelihood of an adverse cardiovascular event in the subject (or population of subjects). The embodiments provided herein also include methods of treating a subject for overweight or obesity, comprising selecting an overweight or obese subject, preferably at increased risk of adverse cardiovascular outcomes or events, including MACE. As provided herein, it has been found that the risk of an adverse cardiovascular event can be reduced in a subject or population by administering naltrexone and bupropion to the subject or population. This is particularly true of subjects that have been identified as being at increased risk of an adverse cardiovascular event. However, even more "normal" subjects not known to have an elevated risk can also be treated and receive the benefit of reducing the predicted likelihood of MACE.

Note that reduction or decrease of risk is most easily seen when observing a population of treated subjects. Thus, for example, one may observe a decrease in predicted likelihood or risk of MACE in a population by comparing actual MACE in that treated population to a comparable untreated population. As used herein, the same conclusion can be drawn for treatment of an individual or subject falling into an at-risk or enhanced risk category, even if rigid statistical correlations cannot be demonstrated for that case where n=1. Nevertheless, likelihood of MACE for an individual subject is considered to be decreased if it is statistically decreased for any population of subjects to which that individual belongs. References herein to reducing or decreasing likelihood of MACE in a subject should be interpreted to encompass decreasing for an individual subject and/or decreasing the risk for a subject population, unless the context clearly dictates otherwise.

Some embodiments provided herein include methods in which the subject has cardiac arrhythmia. Cardiac arrhythmia is a condition in which the electrical activity of the heart is irregular or is faster or slower than normal. In some embodiments, the arrhythmia is tachycardia (e.g., at least 100 beats per minute); some embodiments, the arrhythmia is bradycardia (e.g., less than 60 beats per minute). In some embodiments, the arrhythmia is an irregular heartbeat. In some embodiments, the arrhythmia is fibrillation, such as atrial fibrillation or ventricular fibrillation. In some embodiments, the arrhythmia is not sinus tachycardia. In some embodiments, the cardiac arrhythmia can result in cardiac arrest or can predispose the subject to stroke. Example 2 below summarizes some results of a clinical study that demonstrates that treatment with Naltrexone SR/Bupropion SR decreases the occurrence of MACE in overweight and obese subjects with cardiovascular risk factors, where some of these subjects had cardiac arrhythmia. Briefly stated, fewer subjects in the Naltrexone SR/Bupropion SR treatment group with cardiac arrhythmia experienced a MACE event compared to the placebo with cardiac arrhythmia. The embodiments provided herein include administering naltrexone and bupropion to a subject with cardiac arrhythmia that is at risk of MACE.

Some embodiments provided herein include methods in which the subject is characterized as having depression. For example, the subject can be diagnosed as having clinical depression (major depressive disorder or another form of depression) or can have symptoms consistent with clinical depression. In some embodiments, a subject with depression is taking an antidepressant. In some embodiments, the antidepressant is a selective serine reuptake inhibitor (SSRI) administered according to the standard of care for treating depression. The antidepressant can be one or more of the compounds listed in Table 3. Example 2 below summarizes some results of a clinical study that demonstrates that treatment with Naltrexone SR/Bupropion SR decreases the occurrence of MACE in overweight and obese subjects with cardiovascular risk factors, where some of these subjects had depression. Briefly stated, fewer subjects in the Naltrexone SR/Bupropion SR treatment group with depression experienced a MACE event compared to a placebo group with depression. The embodiments provided herein include administering naltrexone and bupropion to a subject with depression that is at risk of MACE. The embodiments provided herein also include administering naltrexone and bupropion to a subject that is taking an antidepressant preferably an SSRI, such as an antidepressant listed in Table 3 (whether or not that subject has depression).

Some embodiments provided herein include methods in which the subject is being treated according to the standard of care with existing medications, some of which are known to lower risk or likelihood of MACE, including medications to treat diabetes, dyslipidemia, and hypertension. For example, the subject is being treated with a diabetes, dyslipidemia, or hypertension medication listed in Tables 1 and 2. Example 2 below summarizes some results of a clinical study that demonstrates treatment with Naltrexone SR/Bupropion SR decreases the occurrence of MACE in overweight and obese subjects with cardiovascular risk factors, where some of these subjects were being treated according to the standard of care with a diabetes, dyslipidemia, or hypertension medication. Briefly stated, fewer subjects in the Naltrexone SR/Bupropion SR treatment group being treated with such a medication experienced a MACE event compared to the placebo being treated with the same medication. The embodiments provided herein include administering naltrexone and bupropion to a subject that is at risk of MACE and that is being treated according to the standard of care with a diabetes, dyslipidemia, or hypertension medication. The embodiments provided herein also include administering naltrexone and bupropion to a subject that is taking a diabetes, dyslipidemia, or hypertension medication, such as a medication in Tables 1 and 2.

Some embodiments provided herein include methods for preventing or delaying the onset of a major adverse cardiovascular event.

In some embodiments, the methods provided herein can be effective to reduce the risk of one or more major adverse cardiovascular events (MACE) in a subject, to reduce the predicted severity of an adverse cardiovascular event, to decrease the predicted mortality from an adverse cardiovascular event, and combinations thereof. Such a reduction or decrease in risk, predicted severity or predicted mortality can be a reduction of at least or at least about 5%, 10%, 15%, 20%, 25%, 30%, 35%, 40%, 45%, 50%, 60%, 70%, 80%, or 90% in the risk of MACE, predicted severity of an adverse cardiovascular event or predicted mortality from an adverse cardiovascular event, relative to a subject at the same level of risk of MACE, predicted severity of an adverse cardiovascular event or predicted mortality from an adverse cardiovascular event, but who is not receiving treatment by administration of naltrexone and bupropion according to the methods provided herein.

In some embodiments, the methods provided herein can be effective to decrease the progression of cardiovascular disease in a subject. Such a decrease in the progression of cardiovascular disease can be a decrease of at least or at least about 50%, 10%, 15%, 20%, 25%, 30%, 35%, 40%, 45%, 50%, 60%, 70%, 80%, or 90% in the progression of cardiovascular disease, relative to a subject at the same level of cardiovascular disease progression, but who is not receiving treatment by administration of naltrexone and bupropion according to the methods provided herein.

In some embodiments, the methods provided herein can be effective to increase the predicted life expectancy of the subject, or to increase the predicted time period until occurrence of an adverse cardiovascular event. Such an increase in the predicted life expectancy of the subject or the predicted time period until occurrence of an adverse cardiovascular events can be at least or at least about 1 month, 2 months, 3 months, 4 months, 5 months, 6 months, 7 months, 8 months, 9 months, 10 months, 11 months, 12 months, 14 months, 16 months, 18 months, 20 months, or 24 months, relative to a subject at the same level of risk of MACE, but who is not receiving treatment by administration of naltrexone and bupropion according to the methods provided herein.

In some embodiments, the methods provided herein can be effective to increase the effectiveness of a cardiovascular intervention in a subject. Such an increase in the effectiveness of a cardiovascular intervention in a subject can be at least or at least about at least or at least about 5%, 10%, 15%, 20%, 25%, 30%, 35%, 40%/o, 45%, 50%, 60%, 70%, 80%, or 90%, relative to the expected effectiveness of a cardiovascular intervention in a subject at the same level of risk of MACE receiving the same cardiovascular intervention, but who is not receiving treatment by administration of naltrexone and bupropion according to the methods provided herein.

In some embodiments, the methods provided herein can be effective to favorably modulate a diagnostic indicator predictive of a major adverse cardiovascular event. There are a large number of such diagnostic indicators, which include, for example, blood pressure, treadmill testing, troponin testing, fluid volume, cardiac output, ejection fraction, cardiomyopathy, cardiac hypertrophy, ECG abnormalities, external oxygen dependence, diuretic requirements, hospitalization for cardiac insufficiency, unstable plaque, angina, arrhythmias, Q-T interval, elevated triglycerides, elevated LDL, or low HDL; and the like. Such a favorable modulation of a diagnostic indicator predictive of a major adverse cardiovascular event in a subject can be a modulation of at least or at least about at least or at least about 5%, 10%, 15%, 20%, 25%, 30%, 35%, 40%, 45%, 50%, 60%, 70%, 80%, or 90%, relative to the diagnostic indicator predictive of a major adverse cardiovascular event in a subject at the same level of risk of MACE, but who is not receiving treatment by administration of naltrexone and bupropion according to the methods provided herein.

In some embodiments, the methods provided herein can result in the subject's hazard ratio (HR) (comparing risk in treated group versus risk in placebo group per industry standards) of a particular adverse outcome, for example MACE (e.g., one or more of cardiovascular death, non-fatal myocardial infarction, or non-fatal stroke), Four-point Expanded MACE, Five-point Expanded MACE. CV death, nonfatal MI, stroke, fatal stroke, nonfatal stroke, Nonfatal HUSA (hospitalization due to unstable angina), coronary revascularization procedure, and/or all-cause mortality, being less than: 1.9, 1.8, 1.7, 1.6, 1.5, 1.4, 1.3, 1.2, 1.1, and preferably less than 1.0, 0.9, 0.8, 0.7, 0.6, 0.5, 0.4, 0.3, 0.2, 0.1, 0.08, 0.06, 0.04, 0.02, or 0.01. In any of the disclosed embodiments, the hazard radio may be: 1.9, 1.8, 1.7, 1.6, 1.5, 1.4, 1.3, 1.2, 1.1, 1.0, more preferably 0.9, 0.8, 0.7, 0.6, 0.5, 0.4, 0.3, 0.2, 0.1, 0.08, 0.06, 0.04, 0.02 or 0.01, or a range defined by any two of the preceding values.

In some embodiments, the methods provided herein can result in the subject's hazard ratio of a particular adverse outcome being 0.01 to 0.1, 0.1 to 1.9, 0.2 to 1.8, 0.3 to 1.7, 0.4 to 1.6, 0.5 to 1.5, 0.6 to 1.4, 0.7 to 1.3, 0.8 to 1.2, 0.9 to 1.1, 0.1 to 1.0, 0.2 to 1.1, 0.3 to 1.2, 0.4 to 1.3, 0.5 to 1.4, 0.6 to 1.5, 0.7 to 1.6, 0.8 to 1.7, 0.9 to 1.8, or 1.0 to 1.9. In some embodiments, the HR is 0.1 to 0.7. In some embodiments, the HR is 0.1 to 0.8. In some embodiments, the HR is 0.2 to 0.7. In some embodiments, the HR is 0.2 to 1.6. In some embodiments, the HR is 0.2 to 1.9. In some embodiments, the HR is 0.3 to 1.8. In some embodiments, the HR is 0.4 to 0.9. In some embodiments, the HR is 0.4 to 1.2. In some embodiments, the HR is 0.4 to 1.6. In some embodiments, the HR is 0.6 to 1.1.

In any of the disclosed embodiments, one or more improvements provided by the disclosed method (e.g. reduction in the risk of one or more MACE, reduction in the predicted severity of an adverse cardiovascular event, decrease in the predicted mortality from an adverse cardiovascular event, decrease in the progression of cardiovascular disease in a subject, increase in the predicted life expectancy of the subject, or increase in the predicted time period until next occurrence of an adverse cardiovascular event, the increase in the effectiveness of a cardiovascular intervention in a subject, or favorable modulation in a diagnostic indicator predictive of a major adverse cardiovascular event), may continue for a period of time after the discontinuation of the administration of naltrexone and bupropion. In some embodiments, this period of time is, or is at least, 1, 2, 3, 4, 5, or 6 months, or 0.5, 1, 2, 3, 4, or 5 years, or between 1-6 months, 1 month to 1 year, 4 months to 2 years, or 6 months to 5 years.

In some embodiments, the subject experiences change in blood pressure during treatment. In some embodiments, the subject's blood pressure change relative to baseline level is measured at a treatment period selected from 2, 8, 16, 20, 24, 26, 30 or 52 weeks of treatment. In some embodiments, the subjects blood pressure, systolic and/or diastolic blood pressure, is essentially unchanged at one or more treatment periods. In some embodiments, the subjects blood pressure, systolic and/or diastolic blood pressure, is decreased at one or more treatment periods. In some embodiments, the subjects blood pressure, systolic and/or diastolic blood pressure, is increased at one or more treatment periods. In some embodiments, the increase or decrease in blood pressure, systolic and/or diastolic blood pressure, at one or more treatment periods is, or is about, 1%, 2%, 3%, 4%, 5%, 6%, 7%, 8% 9% or 10%, or a range defined by any two of the preceding values. In some embodiments, the increase or decrease in blood pressure, systolic and/or diastolic blood pressure, at one or more treatment periods is, or is about, 0.25 mm Hg, 0.5 mm Hg, 0.75 mm Hg, 1 mm Hg, 1.25 mm Hg, 1.5 mm Hg, 1.75 mm Hg, 2 mmHg, 3 mmHg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, or 15 mm Hg, or a range defined by any two of the preceding values. In some embodiments, the change in blood pressure is a least squares mean change in blood pressure in a population of treated patients relative to placebo treated population. In some embodiments, the subject experiences an increase in blood pressure at one or more treatment periods while experiencing one or more improvements provided by the disclosed methods (e.g. reduction in the risk of one or more MACE, reduction in the predicted severity of an adverse cardiovascular event, decrease in the predicted mortality from an adverse cardiovascular event, decrease in the progression of cardiovascular disease in a subject, increase in the predicted life expectancy of the subject, or increase in the predicted time period until next occurrence of an adverse cardiovascular event, the increase in the effectiveness of a cardiovascular intervention in a subject, or favorable modulation in a diagnostic indicator predictive of a major adverse cardiovascular event). In some embodiments, the increase in blood pressure is an increase in diastolic blood pressure, wherein the increase is 0.25 to 1.5 mm Hg. In some embodiments, the subject experiences an increase in blood pressure at one or more treatment periods while experiencing worsening, rather than one or more improvements provided by the disclosed methods.

In some embodiments, one or more improvements provided by the disclosed method can occur without the subject losing significant weight, in absolute terms or relative to a control population not receiving naltrexone and bupropion (e.g. a placebo control). In some embodiments, one or more improvements provided by the disclosed methods can occur when the subject has lost no weight or has lost less than 5%, 4%, 3%, 2% or 1% of their body weight, in absolute terms or relative to a control. In some embodiments, one or more improvements can be measured or assessed after 16 weeks of treatment, 20 weeks, 24 weeks or 30 weeks, and/or before the subject has lost any weight. In some embodiments, one or more improvements can be measured or assessed before the subject has lost less than 5%, 4%, 3%, 2% or 1% of their body weight, in absolute terms or relative to a control. In some embodiments, the reduction in likelihood of MACE is independent of weight loss.

In some embodiments one or more improvements provided by the disclosed method (e.g. reduction in the risk of one or more MACE, reduction in the predicted severity of an adverse cardiovascular event, decrease in the predicted mortality from an adverse cardiovascular event, decrease in the progression of cardiovascular disease in a subject increase in the predicted life expectancy of the subject, or increase in the predicted time period until next occurrence of an adverse cardiovascular event, the increase in the effectiveness of a cardiovascular intervention in a subject or favorable modulation in a diagnostic indicator predictive of a major adverse cardiovascular event), is seen in a treated patient population as compared to a control population, for example between patients receiving naltrexone and bupropion and patients receiving placebo. In some embodiments, improvement can be observed between the two patient populations in, or in as few as, 12 weeks, 16 weeks, 18 weeks, 20 weeks, 22 weeks, 24 weeks, 26 weeks, 30 weeks or 52 weeks.

In some embodiments, the improvement is a reduction in hazard ratio for, or an increase in time until first incidence of MACE, Four-point Expanded MACE, Five-point Expanded MACE, CV death, nonfatal MI, stroke, fatal stroke, nonfatal stroke, Nonfatal HUSA (hospitalization due to unstable angina), coronary revascularization procedure, and/or all-cause mortality. In any of the disclosed embodiments, the time until first incidence of one or more of MACE. Four-point Expanded MACE. Five-point Expanded MACE, CV death, nonfatal MI, stroke, fatal stroke, nonfatal stroke. Nonfatal HUSA (hospitalization due to unstable angina), coronary revascularization procedure, and/or all-cause mortality is increased. In some embodiments, the time is increased by, or by at least, 8, 10, 12, 14, 16, 18, 20, 30, 40, 50 weeks, or a range defined by any two of the preceding values. In some embodiments, the time is increased by, or by at least, 8 to 50 week, 16 to 30 weeks, 8 to 14 weeks, or 18 to 50 weeks.

Some embodiments relate to methods for advising subjects of the benefits and/or risks of the disclosed compositions, kits, uses, systems and methods, including the reduction in risk or delay in onset of risks identified herein. Subjects can be advised by providing to them or making available to them written information in conjunction with prescribing, receiving, or administering the drugs to the subjects, including providing written or electronic material to the patient or providing all or part of the information in the drug label as approved by a regulatory body. Alternatively, the advising step can occur by advising a caregiver or medical professional, including a physician or pharmacist, who in turn provides the information to the subject.

Some embodiments relate to methods for identifying and/or prescribing methods or treatments disclosed herein to a subject or patient population. Some embodiments relate to methods for monitoring a subject or patient population for one or more of the benefits and/or risks disclosed herein. Subjects or patient populations include any of the subjects or patient populations disclosed herein, including subjects, patient populations and/or subpopulations identified in Tables 5, 6 and 8. The benefit provided by the methods disclosed herein and/or risk assessed include, but are not limited to those disclosed in the various figures and tables disclosed herein. Assessment of an improvement or risk include any common methods of comparing values for a given parameter between treatment groups—for example, the number of subjects that die of a cardiovascular event. Any of the parameters measured for the treatment groups (placebo and naltrexone/bupropion) disclosed herein can be the basis for a benefit or risk. Said advising, prescribing, and monitoring, or combinations thereof, can be in addition to any of the other disclosed embodiments, for example, but not limited to, in addition to embodiments disclosing methods of treatment.

Administration

In some embodiments, naltrexone and/or bupropion is administered once per day. In some embodiments, the naltrexone and/or bupropion is divided into two or more doses, preferably equal doses, and administered more than once per day. In some embodiments, the naltrexone and/or bupropion is divided into unequal doses and administered more than once per day. In some embodiments, the naltrexone and bupropion are divided into a different number of doses and are administered a different number of times per day. In some embodiments, the dose of one of naltrexone or bupropion is divided, while the dose of the other is not.

In some embodiments, one or both of naltrexone and bupropion is administered one, two, three, four, or more times per day. Either or both compounds can be administered less than once per day, for example once every 2, 3, 4, 5, 6, 7, 8, 9, 10, 11, 12, 13, or 14 days, or every 1 or 2 weeks, or a range defined by any two of the preceding values. In some embodiments, the number of administrations per day is constant (e.g., one time per day). In other embodiments, the number of administrations is variable. The number of administrations may change depending on effectiveness of the dosage form, observed side effects, desire to titrate up to a desired dosage, external factors (e.g., a change in another medication), or the length of time that the dosage form has been administered.

In some embodiments, the daily dose of naltrexone can range from about 4 mg to about 50 mg, or about 4 mg to about 32 mg, or about 8 mg to about 32 mg, or about 8 mg to about 16 mg. In some embodiments, the daily dose is about 4 mg, about 8 mg, about 12 mg, about 16 mg, about 32 mg, or about 48 mg of naltrexone, or a range defined by any two of the preceding values. The selection of a particular dosage may be based on the weight of the patient. The selection of a particular dosage may be based on the identity, dosage, and/or dosing schedule of another co-administered compound. However, in some embodiments, it may be necessary to use dosages outside these ranges. In some embodiments, the daily dose is administered in a single oral dosage form. In some embodiments, the daily dose of naltrexone is the same, and in some embodiments, the daily dose is different.

In some embodiments, the daily dose of bupropion can range from about 30 mg to about 500 mg, or about 30 mg to about 360 mg, or about 90 mg to about 360 mg. In some embodiments, the daily dose is about 30 mg, about 90 mg, about 180 mg, about 360 mg, or about 450 mg of bupropion, or a range defined by any two of the preceding values. The selection of a particular dosage may be based on the weight of the patient. The selection of a particular dosage may be based on the identity, dosage and/or dosing schedule of another co-administered compound. However, in some embodiments, it may be necessary to use dosages outside these ranges. In some embodiments, the daily dose is administered in a single oral dosage form. In some embodiments, the daily dose of bupropion is the same, and in some embodiments, the daily dose is different.

The compositions described herein may be distributed, provided to a patient for self-administration, or administered to an individual.

In some embodiments, that naltrexone and/or bupropion is provided or administered as an oral dosage form. In some embodiments, the oral dosage form is in the form of a pill, tablet, core, capsule, caplet, loose powder, solution, or suspension. In a preferred embodiment, the oral dosage form is in the form of a pill, tablet, or capsule. In some embodiments, the combined naltrexone/bupropion therapy is provided in a single oral dosage form. In some embodiments, the oral dosage form is in the form of a trilayer tablet as described in U.S. Patent Publication No. 2008/0113026, which is incorporated herein by reference in its entirety and for all purposes, including without limitation for the purpose of describing trilayer tablets, methods of making and formulating trilayer tablets, and methods of administering them.

In some embodiments, at least one of naltrexone and bupropion is administered with varying frequency during treatment. In some of these embodiments, the varying frequency comprises a decreased frequency over time. For example, one or both of naltrexone and bupropion can be initially administered more than once per day, followed by administration only once per day at a later point in treatment. In some embodiments, the daily dosage of at least one of naltrexone and bupropion is consistent despite the varying frequency of administration. For example, in some embodiments, two tablets of each of naltrexone and bupropion are initially administered twice per day, while four tablets of each of naltrexone and bupropion are administered once per day at a later point in treatment. Alternatively, in some embodiments, one or two tablets of each of naltrexone and bupropion are administered at a later point in treatment, where the one or two tablets have an equivalent total daily dosage as the two tablets each of naltrexone and bupropion initially administered twice per day. In some embodiments, the dose of naltrexone and bupropion is administered in an escalating manner. In one embodiment, 8 mg of naltrexone, and 90 mg of bupropion are administered daily for a first week, 16 mg of naltrexone and 180 mg of bupropion are administered daily for a second week, 24 mg of naltrexone and 270 mg of bupropion are administered daily for a third week, and 32 mg of naltrexone and 360 mg of bupropion are administered daily thereafter.

In some embodiments, at least one of naltrexone or bupropion is in a sustained release or controlled release formulation. For example, sustained release forms of naltrexone are described in U.S. Patent Publication No. 2007/0281021, which is incorporated herein by reference in its entirety and for all purposes, including without limitation for the purpose of describing sustained release forms of naltrexone and bupropion, methods of making and formulating them into suitable dosage forms, and methods of administering them. In some embodiments where one or both of naltrexone and bupropion are administered less than once per day in a controlled release or sustained release (SR) formulation, the dose is selected so that the patient receives a daily dose that is about the same as a daily dose described herein.

In some embodiments, the naltrexone is not a sequestered form of naltrexone. For example, in some embodiments, naltrexone is in a non-sequestered, controlled release formulation. In some embodiments, naltrexone is a non-sequestered, sustained release formulation. In preferred embodiments, at least 50% of the naltrexone is released within 24 hours of administration.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is administered with a physiologically acceptable carrier, diluent, or excipient, or a combination thereof. Non-limiting examples of naltrexone/bupropion combinations, formulations thereof, and methods of administering them are disclosed in U.S. Pat. Nos. 7,375,111 and 7,462,626, both of which are incorporated herein by reference in their entirety and for all purposes, including without limitation for the purpose of describing combinations of naltrexone and bupropion, methods of making and formulating them into suitable dosage forms, and methods of administering them. Reference herein to the use or administration of naltrexone and naltrexone/bupropion combinations is understood to include all modes of administration disclosed or referred to herein, including without limitation separate administration, administration in a single dosage form, administration in the form of salts, and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to bupropion. In some embodiments, naltrexone is administered subsequent to bupropion. In some embodiments, naltrexone and bupropion are co-administered. As used herein, co-administration includes administration in a single dosage form, or separate dosage forms that are administered at, or nearly at, the same time.

In some embodiments, the administration of naltrexone and bupropion is continued for a period of or of about, 1, 2, 3, 4, 6, 8, 10, 12, 16, 20, 24, 36, 48, or 52 weeks, or a range defined by any two of the preceding values. In some embodiments, the administration of naltrexone and bupropion is continued until the reduction in symptoms of a disease, disorder, or condition is stabilized for a period of, or of about, 1, 2, 3, 4, 5, 6, or more weeks, or a range defined by any two of the preceding values. In some embodiments, administration of naltrexone and bupropion is continued until the individual no longer needs a treatment.

In some embodiments. "administering" a drug includes an individual obtaining and taking a drug on their own. For example, in some embodiments, an individual obtains a drug from a pharmacy and self-administers the drug in accordance with the methods provided herein.

In some embodiments, the present invention relates to a kit. The kit may include one or more unit dosage forms comprising naltrexone, bupropion, or naltrexone and bupropion. The unit dosage forms may be of an oral formulation. For example, the unit dosage forms may comprise pills, tablets, or capsules. The kit may include a plurality of unit dosage forms. In some embodiments, the unit dosage forms are in a container. In some embodiments, the dosage forms are single oral dosage forms comprising naltrexone and bupropion or pharmaceutically acceptable salts thereof.

The methods, compositions and kits disclosed herein may include information. The information may be in a form prescribed by a governmental agency regulating the manufacture, use, or sale of pharmaceuticals, which notice is reflective of approval by the agency of the form of the drug for human or veterinary administration. Such information, for example, may be the labeling approved by the U.S. Food and Drug Administration for prescription drugs, or the approved product insert. The information can include required information regarding dose and dosage forms, administration schedules and routes of administration, adverse events, contraindications, warning and precautions, drug interactions, and use in specific populations (see, e.g., 21 C.F.R. § 201.57 which is incorporated herein by reference in its entirety), and in some embodiments is required to be present on or associated with the drug for sale of the drug. Dosage forms comprising a sustained-release naltrexone formulation formulated in a compatible pharmaceutical carrier may also be prepared, placed in an appropriate container, and labeled for treatment of an indicated condition. In some embodiments, a kit is for sale of a prescription drug requiring the approval of and subject to the regulations of a governmental agency, such as the Food and Drug Administration of the United States. In some embodiments, the kit comprises the label or product insert required by the agency, such as the FDA, for sale of the kit to consumers, for example in the U.S.

The information may comprise instructions to administer the unit dosage form at a dosage of about 4 mg, about 8 mg, about 12 mg, about 16 mg, about 32 mg, or about 48 mg of naltrexone or a pharmaceutically acceptable salt thereof. The information may comprise instructions to administer the unit dosage form at a dosage of about 30 mg, about 90 mg, about 180 mg, about 360 mg, or about 450 mg of bupropion or a pharmaceutically acceptable salt thereof. These instructions may be provided in a variety of ways. The information may comprise instructions about when to administer the unit dosage forms. For example, the information may comprise instructions about when to administer the unit dosage forms relative to the administration of another medication or food. In preferred embodiments, the information instructs an individual to take naltrexone, or naltrexone and bupropion, with food, preferably a meal.

Some embodiments include information, preferably printed, that taking naltrexone or a pharmaceutically acceptable salt thereof with food results in an increase in the bioavailability of naltrexone or a pharmaceutically acceptable salt thereof compared to taking the same amount of naltrexone or a pharmaceutically acceptable salt thereof without food. Some embodiments include information, preferably printed, that taking bupropion or a pharmaceutically acceptable salt thereof with food results in an increase in the bioavailability of bupropion or a pharmaceutically acceptable salt thereof compared to taking the same amount of bupropion or a pharmaceutically acceptable salt thereof without food. Some embodiments include information, preferably printed, that taking naltrexone and bupropion, or a pharmaceutically acceptable salts thereof, with food results in an increase in the bioavailability of naltrexone and/or bupropion, or a pharmaceutically acceptable salts thereof, compared to taking the same amount of naltrexone and bupropion, or a pharmaceutically acceptable salts thereof, without food. Some embodiments include information, preferably printed, that taking naltrexone, and/or bupropion or pharmaceutically acceptable salts thereof with food results in fewer or less severe drug associated adverse events than taking the same amount of naltrexone and bupropion, or a pharmaceutically acceptable salts thereof, without food. In some embodiments, the adverse events are gastrointestinal events. In some embodiments, information regarding bioavailability, adverse events, or instructions on administration regimes are provided to a subject, a dosage form comprising the medication described in the information is provided to the subject, and the dosage form is administered in accordance to the information. In some embodiments the subject is a patient in need of the medication. In some embodiments the medication is administered as a therapy for a disease as described herein.

Some embodiments include informing a subject by providing information, preferably printed or electronic, directly or through a medical professional, indicating that treatment with bupropion and naltrexone can reduce the risk or likelihood or incidence of MACE, or any one of the conditions that make up MACE.

Instructions and/or information may be present in a variety of forms, including printed information on a suitable medium or substrate (e.g., a piece or pieces of paper on which the information is printed), computer readable medium (e.g., diskette, CD, etc. on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver or other medical professional involved in treatment of the patient or supply of medication. In some embodiments, the information is provided to a person orally.

Some embodiments comprise a therapeutic package suitable for commercial sale. Non-limiting examples of packs and dispensers as well as oral dosage forms are disclosed in U.S. Patent Publication Nos. 2008/0110792 and 2008/0113026, both of which are hereby incorporated herein by reference in their entirety and for all purposes, including without limitation for the purpose of describing combinations of naltrexone and bupropion, methods of making and formulating them into suitable dosage forms, methods of packing and dispensing them, and methods of administering them.

The information can be associated with the container, for example, by being: written on a label (e.g., the prescription label or a separate label) adhesively affixed to a bottle containing a dosage form described herein: included inside a container as a written package insert, such as inside a box which contains unit dose packets; applied directly to the container such as being printed on the wall of a box; or attached as by being tied or taped, e.g., as an instructional card affixed to the neck of a bottle via a string, cord or other line, lanyard or tether type device. The information may be printed directly on a unit dose pack or blister pack or blister card.

In some embodiments, the methods, treatments and therapies disclosed herein include administration of naltrexone and bupropion plus one or more additional pharmaceutical compounds. In some embodiments a combination selected from one of Tables 1, 2 or 3 are administered to a subject or patient population.

TABLE 1

Combinations of Naltrexone and Bupropion with Anti-hypertensive or Lipid Modifying Drugs Anti-hypertensive Drug Antiadrenergic agent, centrally acting

| | |
|---|---|
| Naltrexone/Bupropion | antiadrenergic gent, centrally acting |
| Naltrexone/Bupropion | clonidine |
| Naltrexone/Bupropion | guanfacine |

Antiadrenergic agent, peripherally acting

| | |
|---|---|
| Naltrexone/Bupropion | antiadrenergic agent, peripherally acting |
| Naltrexone/Bupropion | doxazosin |
| Naltrexone/Bupropion | terazosin |
| Naltrexone/Bupropion | prazosin |

Agents acting on arteriolar smooth muscle

| | |
|---|---|
| Naltrexone/Bupropion | arteriolar smooth muscle agents |
| Naltrexone/Bupropion | hydralazine |
| Naltrexone/Bupropion | minoxidil |

Other Anti-hypertensive

| | |
|---|---|
| Naltrexone/Bupropion | other anti-hypertensive agents |
| Naltrexone/Bupropion | tadalafil |

Diuretics

| | |
|---|---|
| Naltrexone/Bupropion | diuretics |

Low-ceiling diuretics

| | |
|---|---|
| Naltrexone/Bupropion | low-ceiling diuretics |
| Naltrexone/Bupropion | hydrochlorothiazide |
| Naltrexone/Bupropion | chlorothiazide |
| Naltrexone/Bupropion | trichlormethiazide |
| Naltrexone/Bupropion | chlortalidone |
| Naltrexone/Bupropion | indapamide |
| Naltrexone/Bupropion | metolazone |

High-ceiling diuretics

| | |
|---|---|
| Naltrexone/Bupropion | high-ceiling diuretics |
| Naltrexone/Bupropion | furosemide |
| Naltrexone/Bupropion | bumetanide |
| Naltrexone/Bupropion | torasemide |

Potassium-sparing agents

| | |
|---|---|
| Naltrexone/Bupropion | potassium-sparing agents |
| Naltrexone/Bupropion | spironolactone |
| Naltrexone/Bupropion | triamterene |
| Naltrexone/Bupropion | eplerenone |
| Naltrexone/Bupropion | amiloride |

Diuretics and Potassium-sparing agents in combo

| | |
|---|---|
| Naltrexone/Bupropion | diuretics and potassium-sparing agents in combo |
| Naltrexone/Bupropion | hydrochlorothiazide w/ triamterene |
| Naltrexone/Bupropion | spironolactone w/ hydrochlorothiazide |
| Naltrexone/Bupropion | amiloride w/ hydrochlorothiazide |

Beta blockers

| | |
|---|---|
| Naltrexone/Bupropion | beta blockers |
| Naltrexone/Bupropion | metoprolol |
| Naltrexone/Bupropion | carvedilol |
| Naltrexone/Bupropion | atenolol |
| Naltrexone/Bupropion | nebivolol |
| Naltrexone/Bupropion | propranolol |

TABLE 1-continued

Combinations of Naltrexone and Bupropion with Anti-hypertensive or Lipid Modifying Drugs Anti-hypertensive Drug

| | |
|---|---|
| Naltrexone/Bupropion | labetalol |
| Naltrexone/Bupropion | bisoprolol |
| Naltrexone/Bupropion | nadolol |
| Naltrexone/Bupropion | sotalol |
| Naltrexone/Bupropion | acebutolol |
| Naltrexone/Bupropion | pindolol |
| Naltrexone/Bupropion | timolol |

Beta blockers and Thiazides combo

| | |
|---|---|
| Naltrexone/Bupropion | beta blockers and thiazides combo |
| Naltrexone/Bupropion | bisoprolol fumarate w/ hydrochlorothiazide |
| Naltrexone/Bupropion | atenolol w/ hydrochlorothiazide |
| Naltrexone/Bupropion | hydrochlorothiazide w/ metoprolol tartrate |
| Naltrexone/Bupropion | nadolol and bendroflumethiazide |

Beta blockers and other Diuretics

| | |
|---|---|
| Naltrexone/Bupropion | beta blockers and other diuretics |
| Naltrexone/Bupropion | atenolol w/ chlortalidone |

Selective Calcium Channel Blockers with mainly vascular effects

| | |
|---|---|
| Naltrexone/Bupropion | selective calcium channel blockers w/ mainly vascular effects |
| Naltrexone/Bupropion | amlodipine |
| Naltrexone/Bupropion | nifedipine |
| Naltrexone/Bupropion | felodipine |
| Naltrexone/Bupropion | nisoldipine |
| Naltrexone/Bupropion | isradipine |
| Naltrexone/Bupropion | nicardipine |

Selective Calcium Channel Blockers with direct cardiac effects

| | |
|---|---|
| Naltrexone/Bupropion | selective calcium channel blockers w/ direct cardiac effects |
| Naltrexone/Bupropion | diltiazem |
| Naltrexone/Bupropion | verapamil |

ACE Inhibitors, plain or in combination

| | |
|---|---|
| Naltrexone/Bupropion | ACE inhibitors |
| Naltrexone/Bupropion | lisinopril |
| Naltrexone/Bupropion | ramipril |
| Naltrexone/Bupropion | benazepril |
| Naltrexone/Bupropion | enalapril |
| Naltrexone/Bupropion | quinapril |
| Naltrexone/Bupropion | fosinopril |
| Naltrexone/Bupropion | captopril |
| Naltrexone/Bupropion | trandolapril |
| Naltrexone/Bupropion | perindopril |
| Naltrexone/Bupropion | moexipril |
| Naltrexone/Bupropion | lisinopril/hydrochlorothiazide |
| Naltrexone/Bupropion | amlodipine w/ benazepril |
| Naltrexone/Bupropion | benazepril w/ hydrochlorothiazide |
| Naltrexone/Bupropion | enalapril/hydrochlorothiazide |
| Naltrexone/Bupropion | quinapril hcl w/ hydrochlorothiazide |
| Naltrexone/Bupropion | trandolapril w/ verapamil |
| Naltrexone/Bupropion | captopril w/ hydrochlorothiazide |
| Naltrexone/Bupropion | hydrochlorothiazide w/ moexipril |

Angiotensin II Antagonists, plain or in combo

| | |
|---|---|
| Naltrexone/Bupropion | angiotensin II antagonists |
| Naltrexone/Bupropion | losartan |
| Naltrexone/Bupropion | valsartan |
| Naltrexone/Bupropion | olmesartan |
| Naltrexone/Bupropion | irbesartan |
| Naltrexone/Bupropion | telmisartan |
| Naltrexone/Bupropion | candesartan |
| Naltrexone/Bupropion | azilsartan |
| Naltrexone/Bupropion | eprosartan |
| Naltrexone/Bupropion | hydrochlorothiazide w/ losartan |
| Naltrexone/Bupropion | hydrochlorothiazide w/ valsartan |
| Naltrexone/Bupropion | hydrochlorothiazide w/ olmesartan |
| Naltrexone/Bupropion | amlodipine w/ olmesartan |
| Naltrexone/Bupropion | amlodipine w/ valsartan |
| Naltrexone/Bupropion | hydrochlorothiazide w/ telmisartan |
| Naltrexone/Bupropion | amlodipine w/ hydrochlorothiazide/valsartan |
| Naltrexone/Bupropion | hydrochlorothiazide w/ irbesartan |
| Naltrexone/Bupropion | angiotensin II antagonists and diuretics |
| Naltrexone/Bupropion | candesartan hcl |
| Naltrexone/Bupropion | valturna (aliskiren fumarate, valsartan) |
| Naltrexone/Bupropion | amlodipine w/ telmisartan |

Agents acting on the renin-angiotensin system

| | |
|---|---|
| Naltrexone/Bupropion | renin-angiotensin system agents |
| Naltrexone/Bupropion | aliskiren |
| Naltrexone/Bupropion | aliskiren w/ hydrochlorothiazide |
| Naltrexone/Bupropion | rasilez amlo (aliskiren fumarate, amlodipine besilate) |
| Naltrexone/Bupropion | amturnide(aliskiren fumarate, amlodipine besilate, hydrochlorothiazide) |

Lipid Modifying Agents

| | |
|---|---|
| Naltrexone/Bupropion | lipid modifying agents |
| Naltrexone/Bupropion | HMG CoA reductase inhibitors |
| Naltrexone/Bupropion | atorvastatin |
| Naltrexone/Bupropion | cerivastatin |
| Naltrexone/Bupropion | fluvastatin |
| Naltrexone/Bupropion | lovastatin |
| Naltrexone/Bupropion | mevastatin |
| Naltrexone/Bupropion | pitavastatin |
| Naltrexone/Bupropion | pravastatin |
| Naltrexone/Bupropion | rosuvastatin |
| Naltrexone/Bupropion | simvastatin |
| Naltrexone/Bupropion | fibrates |
| Naltrexone/Bupropion | nicotinic acid and derivatives |
| Naltrexone/Bupropion | HMG CoA reductase inhibitors in combination with other lipid modifying agents |
| Naltrexone/Bupropion | bile acid sequestrants |
| Naltrexone/Bupropion | other lipid modifying agents |

TABLE 2

Combinations of Naltrexone and Bupropion with Glucose and Insulin Lowering Drugs Glucose and Insulin Lowering Drugs Insulin and Analogs

| | |
|---|---|
| Naltrexone/Bupropion | insulin |
| Naltrexone/Bupropion | insulin analog |
| Naltrexone/Bupropion | insulin glargine |
| Naltrexone/Bupropion | insulin aspart |
| Naltrexone/Bupropion | insulin lispro |
| Naltrexone/Bupropion | insulin detemir |
| Naltrexone/Bupropion | insulin human w/ insulin human injection, isop. |
| Naltrexone/Bupropion | insulin human |
| Naltrexone/Bupropion | insulin human injection, isophane |
| Naltrexone/Bupropion | novolog mix (insulin aspart, insulin aspart protamine) |
| Naltrexone/Bupropion | insulin glulisine |
| Naltrexone/Bupropion | humalog mix (insulin lispro, insulin lispro protamine suspension) |
| Naltrexone/Bupropion | isophane insulin |
| Naltrexone/Bupropion | insulin human zinc suspension |
| Naltrexone/Bupropion | insulin isophane bovine |
| Naltrexone/Bupropion | insul 30/70 |
| Naltrexone/Bupropion | insulin lispro protamine suspension |
| Naltrexone/Bupropion | insulin porcine zinc suspension |

Blood glucose lowering drugs, excluding Insulin

| | |
|---|---|
| Naltrexone/Bupropion | blood glucose lowering drugs, excluding insulin |
| Naltrexone/Bupropion | metformin |
| Naltrexone/Bupropion | glipizide |
| Naltrexone/Bupropion | glimepiride |
| Naltrexone/Bupropion | sitagliptin |
| Naltrexone/Bupropion | pioglitazone |
| Naltrexone/Bupropion | liraglutide |

TABLE 2-continued

Combinations of Naltrexone and Bupropion with Glucose and Insulin Lowering Drugs Glucose and Insulin Lowering Drugs

| | |
|---|---|
| Naltrexone/Bupropion | glibenclamide |
| Naltrexone/Bupropion | metformin w/ sitagliptin |
| Naltrexone/Bupropion | exenatide |
| Naltrexone/Bupropion | saxagliptin |
| Naltrexone/Bupropion | glibenclamide w/ metformin |
| Naltrexone/Bupropion | metformin w/ pioglitazone |
| Naltrexone/Bupropion | metformin hydrochloride w/ saxagliptin |
| Naltrexone/Bupropion | linagliptin |
| Naltrexone/Bupropion | pramlintide |
| Naltrexone/Bupropion | repaglinide |
| Naltrexone/Bupropion | nateglinide |
| Naltrexone/Bupropion | glipizide/metformin |
| Naltrexone/Bupropion | acarbose |
| Naltrexone/Bupropion | linagliptin w/ metformin |
| Naltrexone/Bupropion | glimepiride w/ pioglitazone |
| Naltrexone/Bupropion | rosiglitazone |
| Naltrexone/Bupropion | metformin w/ rosiglitazone |
| Naltrexone/Bupropion | juvisyne (simvastastatin and sitagliptin) |
| Naltrexone/Bupropion | thiazolidinediones |
| Naltrexone/Bupropion | canagliflozin |
| Naltrexone/Bupropion | dipeptidyl peptidase 4 (dpp-4) inhibitors |
| Naltrexone/Bupropion | miglitol |
| Naltrexone/Bupropion | tolbutamide |

TABLE 3

Combinations of Naltrexone and Bupropion with an Antidepressant

Antidepressant Drugs

SSRI

| | |
|---|---|
| Naltrexone/Bupropion | SSRI |
| Naltrexone/Bupropion | citalopram |
| Naltrexone/Bupropion | dapoxetine |
| Naltrexone/Bupropion | escitalopram |
| Naltrexone/Bupropion | fluoxetine |
| Naltrexone/Bupropion | fluvoxamine |
| Naltrexone/Bupropion | indalpine |
| Naltrexone/Bupropion | paroxetine |
| Naltrexone/Bupropion | sertraline |
| Naltrexone/Bupropion | zimelidine |
| | Other Antidepressants |
| Naltrexone/Bupropion | serotonin-norepinephrine reuptake inhibitors |
| Naltrexone/Bupropion | tricyclic antidepressants |
| Naltrexone/Bupropion | monoamine oxidase inhibitors |
| Naltrexone/Bupropion | Non-SSRI antidepressant |

The term "bupropion" is used in a general way herein to refer to a free base of bupropion, a pharmaceutically acceptable bupropion salt (including anhydrous forms, e.g., anhydrous bupropion), a bupropion metabolite (e.g., hydroxybupropion, threohydrobupropion, and erythrohydrobupropion), a bupropion isomer, or mixtures thereof.

The term "'naltrexone'" is used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, or mixtures thereof.

The term "pharmaceutically acceptable salt," as used herein, refers to a formulation of a compound that does not cause significant irritation to an organism to which it is administered and does not abrogate the biological activity and properties of the compound. Pharmaceutical salts can be obtained by routine experimentation. Non-limiting examples of pharmaceutically acceptable salts include bupropion hydrochloride, radafaxine hydrochloride, naltrexone hydrochloride, and 6-β naltrexol hydrochloride.

Throughout the present disclosure, when a particular compound is mentioned by name, for example, bupropion or naltrexone, it is understood that the scope of the present disclosure encompasses pharmaceutically acceptable salts, esters, amides, or metabolites of the named compound. For example, in any of the embodiments herein, an active metabolite of naltrexone (e.g., 6-β naltrexol) can be used in combination with, or instead of, naltrexone. In any of the embodiments herein, an active metabolite of bupropion, including S,S-hydroxybupropion (i.e., radafaxine), can be used in combination with, or instead of, bupropion.

The term "sustained release," as used herein, has its ordinary meaning as understood by those skilled in the art and thus includes, by way of non-limiting example, the controlled release of a drug from a dosage form over an extended period of time. For example, in some embodiments, sustained-release dosage forms are those that have a release rate that is slower that of a comparable immediate release form, e.g., less than 80% of the release rate of an immediate-release dosage form.

An immediate-release naltrexone formulation appropriate for use as a reference standard is the immediate-release naltrexone formulation, widely available commercially as the REVIA® brand of naltrexone hydrochloride, or an equivalent thereof. An immediate-release bupropion formulation appropriate for use as a reference standard is the immediate-release bupropion formulation, widely available commercially as the WELLBUTRIN® brand of bupropion, or an equivalent thereof. The U.S. government regulates the manner in which prescription drugs can be labeled and thus reference herein to the REVIA® brand of naltrexone hydrochloride and WELLBUTRIN® brand of bupropion have well-known, fixed, and definite meanings to those skilled in the art.

The term "oral dosage form." as used herein, has its ordinary meaning as understood by those skilled in the art and thus includes, by way of non-limiting example, a formulation of a drug or drugs in a form administrable to a human, including pills, tablets, cores, capsules, caplets, loose powder, solutions, and suspensions.

In any of the embodiments described herein, methods of treatment can alternatively be expressed or protected as use claims such as Swiss-type use claims, or composition for use claims. For example, a method of reducing the risk of MACE with a composition can alternatively entail the use of a composition in the manufacture of a medicament for the reducing the risk of MACE, or the use of a composition for the reduction of MACE, or the composition itself for use in the reduction of MACE.

Weight Management Program

In some embodiments, the methods provide herein include a web-based and/or telephone-based weight management program. In some embodiments, each subject is assigned to a health and fitness professional who counsels them online or on the telephone. Additional educational tools can include weekly web-based informational, educational and motivational resources supplemented by video lessons presented at regular intervals. In some embodiments, content for the program consists of: a weekly email that announces the goals for the week, provides motivation, and encourages continued participation; weekly goals (from email) that align with each week's theme, along with a detailed explanation and a strategy for achieving these goals, placed on the program subject pages; three pieces of additional weekly content posted to user pages (tips and educational information) to help subjects reach their weekly goals; motivational messages throughout the week posted on participant pages; triggered event entails sent to users based on behaviors (i.e. absence from program activity, successful logging); video lessons provided on the program site for participants to view and archived for future access: weekly for the first 16 weeks, biweekly for the next 12 weeks, monthly for the remaining duration of the study, and two refresher campaigns that include 4 weekly sessions each year during the third and fourth year of the trial. Video lessons focus on relevant topics and are developed by subject matter experts.

It is understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLES

The examples below are non-limiting and are merely representative of various aspects of the invention.

Example 1 summarizes the protocol for a clinical study demonstrating that treatment with Naltrexone SR/Bupropion SR does not increase or decreases the occurrence of Major Adverse Cardiovascular Events (MACE) in overweight and obese subjects with cardiovascular risk factors.

Example 1

A Multicenter, Randomized, Double-Blind Placebo-Controlled Study Assessing the Occurrence of Major Adverse Cardiovascular Events (MACE) in Overweight and Obese Subjects With Cardiovascular Risk Factors Receiving 32 mg Naltrexone SR/360 mg Bupropion SR ("NB" or "NB32").

Approximately 9,880 subjects are enrolled into a double-blind lead-in period to identify subjects who do not tolerate treatment with low dose NB well or who exhibit other characteristics predictive of lack of compliance. At initiation of the lead-in period, subjects are randomly assigned in a 1:1 ratio to one of two treatment sequences:1 week of active study medication (1 tablet per day) followed by 1 week of placebo (1 tablet per day), or 1 week of placebo followed by 1 week of active study medication. Eligible subjects are subsequently randomized to treatment with either NB32 or placebo in a 1:1 ratio. The duration of the randomized treatment period (or subject follow-up period for those who discontinue study medication early) is estimated to be between 2-4 years for most subjects.

Subject enrollment may occur in two stages, with approximately 6,850 subjects enrolled to support accrual of sufficient events in randomized subjects for the interim analysis, and approximately 3,030 subjects subsequently enrolled to complete the study. Events in randomized subjects from both stages of enrollment support the final analysis. Additional subjects may be recruited if withdrawal rates during the lead-in period are greater than anticipated.

The study consists of three periods (see FIG. 1):
1) Screening Period (starting at Visit 1, Screen, with informed consent): up to 2 weeks to verify eligibility prior to the first dose of study medication in the lead-in period.
2) Lead-in Period (starting at Visit 2, Week −2): double-blind, 2-week period during which the subjects receive treatment according to one of two sequences: 1 week of active study medication (8 mg naltrexone SR/90 mg bupropion SR [NB32]) once a day followed by 1 week of placebo once a day; or 1 week of placebo followed by 1 week of active study medication. Subjects are randomly assigned to NB or placebo for the lead-in period.
3) Treatment Period (starting at Visit 3, Day 1): double-blind, randomized period during which the subjects who completed the lead-in period and satisfied inclusion/exclusion criteria receive active study medication or placebo. The treatment period starts upon randomization at Visit 3 (Day 1).

a) At Visit 6 (Week 16) there is an evaluation of weight loss and blood pressure changes relative to baseline observations. The target weight loss is >5% with expected minimum weight loss at 16 weeks of ≥2%. Subjects should be discontinued from study medication at Week 16 if:
  they have not lost at least 2% of their body weight or
  they are experiencing sustained (e.g., at 2 or more visits) increases in blood pressure (systolic or diastolic) of ≥10 mm Hg. If the Investigator suspects that an elevated blood pressure measurement may be spurious, subjects should not be discontinued until the elevated measurement is confirmed within 4 weeks.

b) All subjects participate in a comprehensive web-based weight management program as detailed above. Subjects participate in the weight management program through completion of study procedures, regardless of whether they are taking study medication.

c) Every other month between visits past Visit 7 (Week 26), subjects are asked to answer specific questions pertaining to compliance and hospitalizations (potential MACE or serious adverse events [SAEs]), using an internet- or telephone-based data collection system.

d) All randomized subjects who discontinue study medication early complete the End-of-Treatment Visit procedures and continue to participate in the study for the remainder of the trial for collection of MACE data. Subjects are asked to come to the study site at their scheduled visits and complete the internet- or telephone-based data collection every other month between visits past Visit 7 (Week 26) even though they are no longer taking study medication.

Subjects must meet all of the following inclusion criteria to be eligible for participation in this study.
1. ≥50 years of age (women) or ≥45 years of age (men);
2. Body mass index (BMI) ≥27 kg/m² and ≤50 kg/m²;
3. Waist circumference ≥88 cm (women) or ≥102 cm (men);
4. At increased risk of adverse cardiovascular outcomes:
  (a) Cardiovascular disease (confirmed diagnosis or at high likelihood of cardiovascular disease) with at least one of the following: history of documented myocardial infarction >3 months prior to screening; history of coronary revascularization (i.e., coronary artery bypass graft surgery, stent placement, percutaneous transluminal coronary angioplasty, or laser atherectomy); history of carotid or peripheral revascularization (i.e., carotid endarterectomy, lower extremity atherosclerotic disease atherectomy, repair of abdominal aorta aneurysm, femoral or popliteal bypass); angina with ischemic changes (resting ECG), ECG changes on a graded exercise test (GXT), or positive cardiac imaging study; ankle brachial index <0.9 (by simple palpation) within prior 2 years; ≥50% stenosis of a coronary, carotid, or lower extremity artery within prior 2 years; and/or
  (b) Type 2 diabetes mellitus with at least 2 of the following: hypertension (controlled with or without pharmacotherapy at <145/95 mm Hg); dyslipidemia requiring pharmacotherapy; documented low HDL cholesterol (<50 mg/dL in women or <40 mg/dL in men) within prior 12 months; current tobacco smoker.

Subjects having the following characteristics are to be excluded: Myocardial infarction within 3 months prior to screening; Angina pectoris Grade III or IV as per the Canadian Cardiovascular Society grading scheme; Clinical history of cerebrovascular disease (stroke); History of tachyarrhythmia other than sinus tachycardia; Blood pressure ≥145/95 mm Hg, irrespective of treatment with antihypertensive agents; Unstable weight within 3 months prior to screening (e.g., weight gain or loss of >3%); Planned bariatric surgery, cardiac surgery, or coronary angioplasty; Severe renal impairment defined by an estimated GFR <30 mL/min; Clinical history of liver failure or documented ALT or AST greater than 3 times the upper limit of normal (ULN); Known infection with HIV or hepatitis; Chronic use or positive screen for opioids; Recent drug or alcohol abuse or dependence (with the exception of nicotine dependence) within 6 months prior to screening; History of seizures (including febrile seizures), cranial trauma, or other conditions that predispose the subject to seizures; History of mania or current diagnosis of active psychosis, active bulimia or anorexia nervosa (binge eating disorder is not exclusionary); At risk for suicide attempts based on the judgment of the Investigator; Acute depressive illness including new onset of depression or acute exacerbation of symptoms (stable subjects on chronic treatment for depression are not excluded); Any condition with life expectancy anticipated to be less than 4 years (e.g., congestive heart failure NYHA Class 3 or 4); History of malignancy within the previous 5 years, with exception of non-melanoma skin cancer or surgically cured cervical cancer; Current use of other bupropion or naltrexone containing products; History of hypersensitivity or intolerance to naltrexone or bupropion; Use of monoamine oxidase inhibitors within 14 days prior to screening; Use of any investigational drug, device, or procedure within 30 days prior to screening; Pregnant or breast-feeding women, or currently trying to become pregnant, or of child-bearing potential (including peri-menopausal women who have had a menstrual period within one year) and not willing to practice birth control; Inability to consistently access broadband internet; Employment by the Sponsor or the study site, or co-habitation with another individual enrolled in the study.

The study medication (NB and placebo) is provided as tablets. Each active tablet contains 8 mg naltrexone SR/90 mg bupropion SR (8/90). All tablets, including placebo, are identical in appearance to maintain blinding. Dose escalation occurs during the first 4 weeks of the treatment period, as shown in the Table 4 below. Doses can be taken with or without food.

Example 2

Example 2 summarizes Contrave cardiovascular (CV) outcome clinical study results demonstrating that treatment with 32 mg naltrexone sustained-release (SR)/360 mg bupropion SR (NB or NB32) does not increase or decreases the occurrence of Major Adverse Cardiovascular Events (MACE) in overweight and obese subjects with cardiovascular risk factors. The general Study patient inclusion criteria are described in the Example 1 and in more detail below. The treatment period is ongoing, and the results reported are interim results.

At Week 16, there was an evaluation of weight loss and blood pressure changes relative to baseline observations. Subjects were to be discontinued from study medication at Week 16 if they had not lost at least 2% of their body weight or they were experiencing consecutive, sustained increases in blood pressure (systolic or diastolic) of ≥10 mm Hg.

Study drug is to be administered, double-blind, for 3 to 4 years (2 weeks lead-in period and 3 to 4 years treatment period). At the time of the interim analysis, mean duration of exposure to study drug was 26.84 weeks for the placebo group and 30.47 weeks for the NB group. Total subject-years on study medication for the placebo and NB groups were 2289 and 2602, respectively.

Primary endpoints include: Time from treatment period randomization to the first confirmed occurrence of MACE, defined as CV death (including fatal MI and fatal stroke), nonfatal MI, and nonfatal stroke. Secondary endpoints include: Time from treatment period randomization to the first confirmed occurrence of four-point expanded MACE, defined as CV death (including fatal MI, fatal stroke, and fatal HUSA), nonfatal MI, nonfatal stroke, or nonfatal HUSA; Time from treatment period randomization to the confirmed occurrence of CV death (including fatal MI, fatal stroke); Time from treatment period randomization to the first confirmed occurrence of MI (nonfatal or fatal); Time from treatment period randomization to the first confirmed occurrence of stroke (nonfatal or fatal); Other endpoints include: Time from treatment period randomization to the confirmed occurrence of death from any cause; Time from treatment period randomization to the first confirmed occurrence of HUSA (nonfatal or fatal); Time from treatment period randomization to the first occurrence of coronary revascularization procedure; Percent change in body weight from baseline to Week 52; Proportion of subjects achieving ≥10% body weight loss from baseline at Week 52; Change in blood pressure from baseline to Week 52.

Overall, 13,192 subjects were screened for eligibility, of which 10,504 were enrolled into the lead-in period. A total of 8910 subjects who completed the lead-in period were subsequently randomized into the treatment period and

TABLE 4

| Dose | Lead-in Period | | Treatment Period | | | |
|---|---|---|---|---|---|---|
| | | | Week 1 | Week 2 | Week 3 | Week 4 through |
| Schedule | Week −2 | Week −1 | (Days 1-7) | (Days 8-14) | (Days 15-21) | end of study |
| Total Daily Dose* | 8/90 NB | 8/90 NB | 8/90 NB | 16/180 NB | 24/270 NB | 32/360 NB |
| Morning | 1 tab NB or PBO | 1 tab NB or PBO | 1 tab NB or PBO | 1 tab NB or PBO | 2 tabs NB or PBO | 2 tabs NB or PBO |
| Evening | — | — | — | 1 tab NB or PBO | 1 tab NB or PBO | 2 tabs NB or PBO |

*Doses shown are of naltrexone SR bupropion SR (NB): tab = tablet: PBO = placebo.

received at least one dose of treatment period study medication (4450 to placebo and 4454 to NB). As of the 6 Nov. 2013 data cutoff for the interim analysis, 1201 (placebo) and 1708 (NB) subjects were continuing treatment with study medication. The majority of the subjects in the ITT Population (95.2%) continued to be followed for MACE while 4.8% were classified as non-retainable for MACE follow-up because they revoked their consent or became lost to follow-up. Importantly, vital status checks using public records were performed for all subjects who were classified as non-retainable for MACE follow-up. Of the 428 subjects who were classified as non-retainable for MACE follow-up, vital status was obtained for 359 subjects leaving 69 subjects (0.8% of the ITT Population) with no vital status (either not obtained or pending) at the time of this interim analysis. The most common reason for discontinuation of study medication during the treatment period for NB was due to an AE (7.4% placebo, 26.7% NB) and for placebo was not meeting Week 16 continuation of treatment criteria (40.7% placebo, 14.2% NB). All other reasons for discontinuation of study medication were balanced between treatment groups.

Demographic and Baseline Body Mass Characteristics

Demographic and baseline characteristics for subjects in the ITT Population are presented in Table 5. The majority of subjects were female (54.5%), White (83.5%), and not Hispanic or Latino (93.5%). Mean age was 61.0 years. Mean baseline body weight (106.0 kg), BMI (37.3 kg/m$_2$), and waist circumference (119.5 cm) were consistent with the criteria for overweight and obese.

The majority of subjects had T2DM (85.2%) with a smaller proportion having a history of CV disease (CVD, 32.1%). Treatment assignment was balanced within the primary baseline risk groups with an overall distribution of 67.8%, 14.8%, and 17.3% for T2DM only, CVD only, or T2DM with CVD, respectively.

Among subjects with T2DM, the median duration of T2DM was 7.7 years with 58.9% reporting durations of ≥6 years. Mean baseline HbA1c was 7.4%, and 52.7% had an HbA1c≥7%. Antidiabetic medication use at baseline was 78.7% among all subjects in the ITT Population, which reflected primarily metformin use (63.9%). Subjects with T2DM were not required to have an HbA1c value within a specified range for inclusion in the study and there were no restrictions on antidiabetic medications.

The incidence of subjects with hypertension at baseline was 92.9%. Antihypertension medication use at baseline was 93.4%, which reflected primarily angiotensin-converting enzyme inhibitors (ACEI)/angiotensin II receptor blocker (ARB) use (78.0%). Similarly, 91.8% of the subjects reported dyslipidemia at baseline. Lipid altering medication use at baseline was 88.4%, which was mostly attributed to statin (HMG-CoA reductase inhibitor) use (80.4%). The incidence of subjects who were current tobacco smokers at screening was 9.2% and comparable between treatment groups. The CV related baseline conditions, including laboratory values and associated medication use, were comparable between treatment groups and indicate that the subjects, while exhibiting increased CV risk, were also treated for associated comorbidities according to standard of care.

Depression at baseline was experienced by 23.0% of the population. Antidepressant medication use was 24.4% among all subjects in the ITT Population, which was attributed mostly to SSRI use (15.6%). The incidence of subjects with renal impairment (eGFR <90 mL/min) at baseline was 26.9%.

Demographics and baseline characteristics were balanced between treatment groups. There were no unexpected differences in the incidences and pattern of demographic and baseline characteristics among the CV risk groups.

TABLE 5

Demographic and Baseline Characteristics: ITT Population

| Variable | Placebo (N = 4450) | NB (N = 4455) | Total (N = 8905) |
|---|---|---|---|
| Age (yrs) | | | |
| n | 4450 | 4455 | 8905 |
| Mean (SD) | 60.9 (7.38) | 61.1 (7.27) | 61.0 (7.33) |
| Median | 61.0 | 61.0 | 61.0 |
| Range (min, max) | 45.0, 85.0 | 45.0, 86.0 | 45.0, 86.0 |
| Age (yrs) Category, n (%) | | | |
| <65 | 3053 (68.6%) | 2973 (66.7%) | 6026 (67.7%) |
| ≥65 | 1397 (31.4%) | 1482 (33.3%) | 2879 (32.3%) |
| Sex, n (%) | | | |
| Male | 2031 (45.6%) | 2018 (45.3%) | 4049 (45.5%) |
| Female | 2419 (54.4%) | 2437 (54.7%) | 4856 (54.5%) |
| Race, n (%) | | | |
| White | 3698 (83.1%) | 3738 (83.9%) | 7436 (83.5%) |
| Non-White | 750 (16.9%) | 716 (16.1%) | 1466 (16.5%) |
| American Indian or Alaska Native | 20 (0.4%) | 11 (0.2%) | 31 (0.3%) |
| Asian | 27 (0.6%) | 19 (0.4%) | 46 (0.5%) |
| Black or African American | 648 (14.6%) | 656 (14.7%) | 1304 (14.6%) |
| Native Hawaiian or Other Pacific Islander | 6 (0.1%) | 6 (0.1%) | 12 (0.1%) |
| Other | 49 (1.1%) | 24 (0.5%) | 73 (0.8%) |
| Missing | 2 (<0.1%) | 1 (<0.1%) | 3 (<0.1%) |
| Ethnicity, n (%) | | | |
| Hispanic or Latino | 291 (6.5%) | 280 (6.3%) | 571 (6.4%) |
| Not Hispanic or Latino | 4156 (93.4%) | 4173 (93.7%) | 8329 (93.5%) |
| Missing | 3 (<0.1%) | 2 (<0.1%) | 5 (<0.1%) |

TABLE 5-continued

Demographic and Baseline Characteristics: ITT Population

| Variable | Placebo (N = 4450) | NB (N = 4455) | Total (N = 8905) |
|---|---|---|---|
| Height (cm) | | | |
| n | 4450 | 4455 | 8905 |
| Mean (SD) | 169.0 (10.01) | 168.8 (10.00) | 168.9 (10.01) |
| Median | 168.1 | 168.0 | 168.0 |
| Range (min, max) | 123.2, 213.0 | 125.0, 205.7 | 123.2, 213.0 |
| Weight (kg) | | | |
| n | 4450 | 4455 | 8905 |
| Mean (SD) | 106.3 (19.18) | 105.6 (19.09) | 106.0 (19.14) |
| Median | 104.5 | 103.9 | 104.1 |
| Range (min, max) | 60.0, 181.9 | 61.2, 184.3 | 60.0, 184.3 |
| BMI (kg/m$^2$) | | | |
| n | 4450 | 4453 | 8903 |
| Mean (SD) | 37.4 (5.44) | 37.2 (5.26) | 37.3 (5.35) |
| Median | 36.7 | 36.6 | 36.6 |
| Range (min, max) | 26.6, 50.8 | 27.0, 50.4 | 26.6, 50.8 |
| BMI Category (kg/m$^2$), n (%) | | | |
| BMI <35 | 1719 (38.6%) | 1691 (38.0%) | 3410 (38.3%) |
| BMI ≥35 and <40 | 1383 (31.1%) | 1477 (33.2%) | 2860 (32.1%) |
| BMI ≥40 | 1348 (30.3%) | 1285 (28.9%) | 2633 (29.6%) |
| Waist Circumference (cm) | | | |
| n | 4450 | 4452 | 8902 |
| Mean (SD) | 119.6 (13.30) | 119.4 (13.36) | 119.5 (13.33) |
| Median | 118.5 | 118.0 | 118.1 |
| Range (min, max) | 88.0, 195.0 | 88.0, 223.4 | 88.0, 223.4 |
| CV Risk Croup, n (%) | | | |
| CV Disease | 1447 (32.5%) | 1414 (31.7%) | 2861 (32.1%) |
| CV Disease without T2DM | 646 (14.5%) | 671 (15.1%) | 1317 (14.8%) |
| CV Disease with T2DM | 801 (18.0%) | 743 (16.7%) | 1544 (17.3%) |
| T2DM | 3803 (85.5%) | 3783 (84.9%) | 7586 (85.2%) |
| T2DM without CV Disease | 3002 (67.5%) | 3040 (68.2%) | 6042 (67.8%) |
| No CV Disease or T2DM | 1 (<0.1%) | 1 (<0.1%) | 2 (<0.1%) |
| Current Smoker, n (%) | 414 (9.3%) | 405 (9.1%) | 819 (9.2%) |
| Hypertension, n (%) | 4114 (92.4%) | 4160 (93.4%) | 8274 (92.9%) |
| Dyslipidemia, n (%) | 4070 (91.5%) | 4102 (92.1%) | 8172 (91.8%) |
| hsCRP (mg/L) (NR: 0-3 mg/L) | | | |
| n | 4445 | 4449 | 8894 |
| Mean (SD) | 5.2 (8.01) | 5.0 (6.57) | 5.1 (7.32) |
| Median | 2.9 | 2.9 | 2.9 |
| Range (min, max) | 0.1, 139.3 | 0.1, 97.6 | 0.1, 139.3 |
| Total Cholesterol (mg/dL) (NR: <200 mg/dL) | | | |
| n | 4446 | 4449 | 8895 |
| Mean (SD) | 172.8 (42.33) | 171.3 (41.37) | 172.1 (41.86) |
| Median | 165.0 | 165.0 | 165.0 |
| Range (min, max) | 78.0, 588.0 | 60.0, 630.0 | 60.0, 630.0 |
| HDL Cholesterol (mg/dL) (NR: >60 mg/dL) | | | |
| n | 4447 | 4449 | 8896 |
| Mean (SD) | 46.6 (12.67) | 46.3 (12.74) | 46.5 (12.70) |
| Median | 45.0 | 45.0 | 45.0 |
| Range (min, max) | 5.0, 142.0 | 14.0, 126.0 | 5.0, 142.0 |
| LDL Cholesterol (mg/dL) (NR: <130 mg/dL) | | | |
| n | 4445 | 4448 | 8893 |
| Mean (SD) | 88.8 (35.01) | 87.5 (33.35) | 88.1 (34.20) |
| Median | 82.0 | 82.0 | 82.0 |
| Range (min, max) | 11.0, 380.0 | 12.0, 268.0 | 11.0, 380.0 |
| Triglycerides (mg/dL) (NR: <150 mg/dL) | | | |
| n | 4446 | 4449 | 8895 |
| Mean (SD) | 195.6 (144.91) | 196.6 (141.65) | 196.1 (143.28) |
| Median | 166.0 | 166.0 | 166.0 |
| Range (min, max) | 32.0, 5167.0 | 27.0, 3520.0 | 27.0, 5167.0 |
| Antihypertensive Medication Use, n (%) | 4145 (93.1%) | 4176 (93.7%) | 8321 (93.4%) |
| Beta Blocking Agent | 1730 (38.9%) | 1793 (40.2%) | 3523 (39.6%) |

TABLE 5-continued

Demographic and Baseline Characteristics: ITT Population

| Variable | Placebo (N = 4450) | NB (N = 4455) | Total (N = 8905) |
|---|---|---|---|
| Diuretic | 1439 (32.3%) | 1501 (33.7%) | 2940 (33.0%) |
| ACEI/ARB | 3453 (77.6%) | 3491 (78.4%) | 6944 (78.0%) |
| Calcium Channel Blocker | 858 (19.3%) | 916 (20.6%) | 1774 (19.9%) |
| Lipid Altering Medication Use, n (%) | 3925 (88.2%) | 3951 (88.7%) | 7876 (88.4%) |
| Statins | 3568 (80.2%) | 3590 (80.6%) | 7158 (80.4%) |
| Duration of T2DM (years) | | | |
| n | 3727 | 3699 | 7426 |
| Mean (SD) | 9.5 (7.64) | 9.5 (7.42) | 9.5 (7.53) |
| Median | 7.6 | 7.8 | 7.7 |
| Range (min, max) | 0.0, 50.5 | 0.0, 69.0 | 0.0, 69.0 |
| Duration of T2DM Category, n (%) | | | |
| <6 years | 1561 (41.9%) | 1494 (40.4%) | 3055 (41.1%) |
| ≥6 years | 2166 (58.1%) | 2205 (59.6%) | 4371 (58.9%) |
| HbA1c (%) | | | |
| n | 3799 | 3779 | 7578 |
| Mean (SD) | 7.5 (1.57) | 7.4 (1.47) | 7.4 (1.52) |
| Median | 7.1 | 7.0 | 7.0 |
| Range (min, max) | 4.1, 16.0 | 4.5, 15.3 | 4.1, 16.0 |
| HbA1c Category, n (%) | | | |
| <7% | 1766 (46.5%) | 1818 (48.1%) | 3584 (47.3%) |
| ≥7% | 2033 (53.5%) | 1961 (51.9%) | 3994 (52.7%) |
| Antidiabetic Medication Use, n (%) | 3518 (79.1%) | 3493 (78.4%) | 7011 (78.7%) |
| Insulin | 1045 (23.5%) | 1051 (23.6%) | 2096 (23.5%) |
| Thiazolidinediones | 353 (7.9%) | 324 (7.3%) | 677 (7.6%) |
| Metformin | 2866 (64.4%) | 2822 (63.3%) | 5688 (63.9%) |
| GLP-1/DPP-IV | 912 (20.5%) | 940 (21.1%) | 1852 (20.8%) |
| Sulfonylurea | 1174 (26.4%) | 1226 (27.5%) | 2400 (27.0%) |
| Depression, n (%) | 1009 (22.7%) | 1039 (23.3%) | 2048 (23.0%) |
| Antidepressant Medication Use, n (%) | 1072 (24.1%) | 1100 (24.7%) | 2172 (24.4%) |
| SSR1 | 671 (15.1%) | 720 (16.2%) | 1391 (15.6%) |
| eGFR Category, n (%) | | | |
| <90 mL/min | 1174 (26.4%) | 1220 (27.4%) | 2394 (26.9%) |
| ≥90 mL/min | 3275 (73.6%) | 3234 (72.6%) | 6509 (73.1%) |

Abbreviations:
ACEI-angiotensin-converting enzyme inhibitors;
ARB = angiotensin II receptor blocker;
BMI = body mass index;
CV = cardiovascular;
eGFR = estimated glomerular filtration rate;
hsCRP = high-sensitivity C reactive protein;
DPP-IV = dipeptidyl peptidase IV;
GLP-1 = glucagon-like peptide 1;
HbA1c = hemoglobin A1c;
NB = naltrexone SR 32 mg/bupropion SR 360 mg;
NR = normal range:
SSRI = selective serotonin reuptake inhibitor:
T2DM = type 2 diabetes mellitus.

Medical History

To qualify for entry into the study, subjects were to be at increased risk of CV outcomes by either having CV disease, T2DM, or both as defined in inclusion criterion 4 of the protocol set forth in Example 1. A summary of CV medical history for the ITT Population based on the requirements set forth in inclusion criterion 4 of the protocol is provided in Table 6. To be included in the CV disease risk group "CV disease," subjects were to have at least one of the following: history of MI >3 months prior to screening (13.3%); coronary, carotid or peripheral revascularization (25.9%, 0.9%, and 0.7%, respectively); angina with ischemic changes. ECG changes on a graded exercise test, or positive cardiac imaging study (3.8%); ankle brachial index <0.9 within prior 2 years (0.6%); or ≥50% stenosis of a coronary, carotid, or lower extremity artery within prior 2 years (3.6%, 0.7%, and 0.2%, respectively).

To be included in the CV disease risk group "T2DM," subjects were to have T2DM (85.2%) with at least two of the following: history of hypertension (92.9%), dyslipidemia requiring pharmacotherapy (91.8%), documented low HDL within the prior 12 months (29.4%), or was a current smoker (9.2%).

CV medical history was balanced between treatment groups. The incidences and pattern of CV medical history for each CV risk group were expected for a population with CV disease, T2DM, or both.

TABLE 6

Cardiovascular Medical History: ITT Population

|  | Placebo (N = 4450) n (%) | NB (N = 4455) n (%) | Total (N = 8905) n (%) |
|---|---|---|---|
| History of MI >3 months prior to screening | 589 (13.2%) | 592 (13.3%) | 1181 (13.3%) |
| History of coronary revascularizations | 1170 (26.3%) | 1138 (25.5%) | 2308 (25.9%) |
| History of carotid revascularization | 55 (1.2%) | 27 (0.6%) | 82 (0.9%) |
| History of peripheral revascularization | 35 (0.8%) | 27 (0.6%) | 62 (0.7%) |
| Angina with ischemic changes (resting ECG), ECG changes on a graded exercise test, or positive cardiac imaging study | 153 (3.5%) | 186 (4.2%) | 339 (3.8%) |
| Ankle brachial index <0.9 (by simple palpation) within prior 2 years | 24 (0.5%) | 29 (0.7%) | 53 (0.6%) |
| ≥50% stenosis of a coronary artery within prior 2 years | 160 (3.6%) | 157 (3.6%) | 317 (3.6%) |
| ≥50% stenosis of a carotid artery within prior 2 years | 32 (0.7%) | 28 (0.6%) | 60 (0.7%) |
| ≥50% stenosis of a lower extremity artery within prior 2 years | 5 (0.1%) | 11 (0.3%) | 16 (0.2%) |
| T2DM | 3803 (85.5%) | 3783 (84.9%) | 7586 (85.2%) |
| History of hypertension (<145/95 mmHg with or >140/90 and <145/95 mmHg without pharmacotherapy) | 4114 (92.5%) | 4160 (93.4%) | 8274 (92.9%) |
| Dyslipidemia requiring pharmacotherapy | 4070 (91.5%) | 4102 (92.1%) | 8172 (91.8%) |
| Documented low HDL (<50 mg/dL in women and <40 mg/dL in men) within the prior 12 months | 1324 (29.8%) | 1296 (29.1%) | 2620 (29.4%) |
| Current smoker | 414 (9.3%) | 405 (9.1%) | 819 (9.2%) |

Abbreviations:
ECG = electrocardiogram;
HDL = high density lipoprotein;
NB = naltrexone SR 32 mg/bupropion SR 360 mg:
T2DM = type 2 diabetes mellitus.

Analyses of Body Weight and Blood Pressure

Overall, mean weight loss was consistently 2% to 3% greater for NB than placebo (FIG. 3). The clinically and statistically meaningful weight loss was further demonstrated by the higher proportion of subjects achieving ≥10% weight loss from baseline to Week 52 with NB (12.3%) compared to placebo (3.3%); odds ratio 4.13 (p<0.0001). The weight loss observed in this study is consistent with weight loss in subjects with T2DM in previous NB studies, but the absolute and placebo-corrected weight loss is less than observed for the non-diabetic population in previous studies with NB.

In the NB group, blood pressure values were approximately 0.5 mm Hg higher than placebo at most time points, which peaked at Week 8 with a treatment difference of approximately 1 mm Hg that resolved by Week 16.

Safety Results:

Vital Signs

A slightly higher proportion of the subjects with sustained systolic blood pressure increases from baseline were in the NB group. Of the few subjects with sustained systolic blood pressure in the ≥160 mm Hg and ≥180 mm Hg categories, a slightly higher proportion of subjects were in NB and outliers were observed both before and after Week 16. A relatively small proportion of subjects in the NB group had sustained increases in diastolic blood pressure from baseline. Of the few subjects with sustained diastolic outlier blood pressures of ≥100 mm Hg, a slightly higher proportion were in the NB group with the difference between treatments most apparent after Week 16. There were no meaningful differences in the range of maximum change between treatments when evaluated by baseline blood pressure categories.

Slight trends in sustained increases ≥10 bpm in heart rate were observed before Week 16 (slightly higher NB) and after Week 16 (slightly higher placebo), but overall the results were similar between treatments. There was no difference in the overall proportion of subjects with heart rate outlier values ≥100 bpm or ≥110 bpm. There were no meaningful differences in the range of maximum change between treatments when evaluated by baseline heart rate category.

Study Outcome Results and Tabulations of Individual Subject Data

Analysis of MACE and Other Outcome Measures

Primary MACE Analysis

The incidence of first MACE for the ITT Population is presented in Table 7. The total subject-years at risk was similar between the treatment groups. The background MACE rate was 1.3% (placebo group), consistent with the intended target of enrolling subjects with a background MACE rate of 1-1.5%.

Fewer subjects treated with NB (35, 0.8%) experienced a primary endpoint event compared to placebo (59, 1.3%); HR (95% CI) 0.59 (0.39-0.90). The incidence of the individual MACE components of CV death and nonfatal MI was lower for the NB group than placebo, and the incidence of the MACE component nonfatal stroke was similar between groups.

These results clearly meet the pre-specified requirement set forth by the FDA of excluding a HR of 2.0. Furthermore, the favorable point estimate and upper bound of the 95% CI of less than 1.0 indicate that the risk of MACE with NB is not elevated compared to placebo. Separation of the primary endpoint results by treatment occurred early and was favorable for NB throughout the assessment period (FIG. 2).

TABLE 7

Incidence of First MACE: ITT Population

|  | Placebo (N = 4450) | NB (N = 4455) |
|---|---|---|
| MACE, n (%) of Subjects | 59 (1.3%) | 35 (0.8%) |
| CV Death | 16 (0.4%) | 5 (0.1%) |
| Nonfatal MI | 33 (0.7%) | 23 (0.5%) |
| Nonfatal Stroke | 10 (0.2%) | 7 (0.2%) |
| Total Subject-years at Risk | 4757.7 | 4769.0 |
| HR (95% CI)[1] |  | 0.59 (0.39, 0.90) |
| p-value[2] |  | <0.0001 |

Abbreviations:
CI = confidence interval;
CV = cardiovascular;
HR = hazard ratio;
MACE = major adverse cardiovascular events;
MI = myocardial infarction;
NB = naltrexone SR 32 mg/bupropion SR 360 mg.
[1] Based on Cox proportional hazards model with treatment as a factor.
[2] p-value for testing the null hypothesis of HR ≥2 vs. one-sided alternative.

Primary MACE Subgroup Analyses

The primary outcome variable (time to first MACE) was evaluated by the following demographic variables and baseline characteristics: CV risk group, age category, sex, race grouping, ethnicity, BMI category, smoking status, HbA1c category, study medication class, duration of T2DM category, and renal impairment category. These analyses were conducted to explore potential variation in the treatment effect.

The HRs for the incidence of first MACE by subgroup are presented in Table 8 for the ITT Population. The risk for MACE with NB relative to placebo by subgroup was generally similar for the PP Population.

TABLE 8

Incidence of First MACE by Subgroup: ITT Population

| Subgroup | Treatment | N | n (%) | HR (95% CI)[1] |
|---|---|---|---|---|
| CV Risk Group[2] |  |  |  | p = 0.5974[3] |
| CV w/o T2DM | Placebo | 646 | 14 (2.2%) |  |
|  | NB | 671 | 6 (0.9%) | 0.41 (0.16, 1.07) |
| CV w/ T2DM | Placebo | 801 | 25 (3.1%) |  |
|  | NB | 743 | 14 (1.9%) | 0.56 (0.29, 1.09) |
| T2DM w/o CV | Placebo | 3002 | 20 (0.7%) |  |
|  | NB | 3040 | 15 (0.5%) | 0.74 (0.38, 1.45) |
| Age Category |  |  |  | p = 0.4037[3] |
| <65 years | Placebo | 3053 | 35 (1.1%) |  |
|  | NB | 2973 | 23 (0.8%) | 0.67 (0.40, 1.14) |
| ≥65 years | Placebo | 1397 | 24 (1.7%) |  |
|  | NB | 1482 | 12 (0.8%) | 0.46 (0.23, 0.94) |
| Sex |  |  |  | p = 0.1216[3] |
| Male | Placebo | 2031 | 36 (1.8%) |  |
|  | NB | 2018 | 16 (0.8%) | 0.43 (0.23, 0.78) |
| Female | Placebo | 2419 | 23 (1.0%) |  |
|  | NB | 2437 | 19 (0.8%) | 0.83 (0.45, 1.53) |
| Race Grouping[4] |  |  |  | p = 0.5239[3] |
| White | Placebo | 3698 | 47 (1.3%) |  |
|  | NB | 3738 | 29 (0.8%) | 0.62 (0.39, 0.99) |
| Non-White | Placebo | 750 | 12 (1.6%) |  |
|  | NB | 716 | 5 (0.7%) | 0.43 (0.15, 1.23) |
| Ethnicity[4] |  |  |  | p = 0.0976[3] |
| Hispanic or Latino | Placebo | 291 | 3 (1.0%) |  |
|  | NB | 280 | 1 (0.4%) | 0.00 (0.00, N/A) |
| Not Hispanic of Latino | Placebo | 4156 | 55 (1.3%) |  |
|  | NB | 4173 | 34 (0.8%) | 0.63 (0.41, 0.96) |
| BMI Category[4] |  |  |  | p = 0.1338[3] |
| <35 kg/m$^2$ | Placebo | 1719 | 22 (1.3%) |  |
|  | NB | 1691 | 11 (0.7%) | 0.49 (0.23, 1.03) |
| ≥35 to <40 kg/m$^2$ | Placebo | 1383 | 18 (1.3%) |  |
|  | NB | 1477 | 7 (0.5%) | 0.35 (0.14, 0.83) |
| ≥40 kg/m$^2$ | Placebo | 1348 | 19 (1.4%) |  |
|  | NB | 1285 | 17 (1.3%) | 0.98 (0.51, 1.88) |
| Smoking Status |  |  |  | p = 0.0241[3] |
| No | Placebo | 4036 | 49 (1.2%) |  |
|  | NB | 4050 | 34 (0.8%) | 0.69 (0.44, 1.07) |
| Yes | Placebo | 414 | 10 (2.4%) |  |
|  | NB | 405 | 1 (0.2%) | 0.10 (0.01, 0.77) |
| HbA1c Category[4] |  |  |  | p = 0.5747[3] |
| <7% | Placebo | 1766 | 13 (0.7%) |  |
|  | NB | 1818 | 10 (0.6%) | 0.78 (0.34, 1.78) |
| ≥7% | Placebo | 2033 | 32 (1.6%) |  |
|  | NB | 1961 | 19 (1.0%) | 0.59 (0.33, 1.04) |
| Antihypertensive Medication Use |  |  |  | p = 0.6747[3] |
| No | Placebo | 305 | 3 (1.0%) |  |
|  | NB | 279 | 1 (0.4%) | 0.37 (0.04, 3.55) |
| Yes | Placebo | 4145 | 56 (1.4%) |  |
|  | NB | 4176 | 34 (0.8%) | 0.60 (0.39, 0.92) |

TABLE 8-continued

Incidence of First MACE by Subgroup: ITT Population

| Subgroup | Treatment | N | n (%) | HR (95% CI)[1] |
|---|---|---|---|---|
| Beta Blocking Agent | | | | p = 0.3764[3] |
| No | Placebo | 2720 | 23 (0.8%) | |
| | NB | 2662 | 16 (0.6%) | 0.73 (0.38, 1.37) |
| Yes | Placebo | 1730 | 36 (2.1%) | |
| | NB | 1793 | 19 (1.1%) | 0.49 (0.28, 0.87) |
| Diuretic | | | | p = 0.5307[3] |
| No | Placebo | 3011 | 30 (1.0%) | |
| | NB | 2954 | 20 (0.7%) | 0.66 (0.37, 1.17) |
| Yes | Placebo | 1439 | 29 (2.0%) | |
| | NB | 1501 | 15 (1.0%) | 0.50 (0.27, 0.94) |
| ACEI/ARB | | | | p = 0.5138[3] |
| No | Placebo | 997 | 12 (1.2%) | |
| | NB | 964 | 5 (0.5%) | 0.43 (0.15, 1.22) |
| Yes | Placebo | 3453 | 47 (1.4%) | |
| | NB | 3491 | 30 (0.9%) | 0.62 (0.39, 0.99) |
| Calcium Channel Blocker | | | | p = 0.6245[3] |
| No | Placebo | 3592 | 45 (1.3%) | |
| | NB | 3539 | 28 (0.8%) | 0.62 (0.38, 1.00) |
| Yes | Placebo | 858 | 14 (1.6%) | |
| | NB | 916 | 7 (0.8%) | 0.48 (0.19, 1.19) |
| Antidiabetic Medication Use | | | | p = 0.1817[3] |
| No | Placebo | 932 | 21 (2.3%) | |
| | NB | 962 | 8 (0.8%) | 0.37 (0.17, 0.84) |
| Yes | Placebo | 3518 | 38 (1.1%) | |
| | NB | 3493 | 27 (0.8%) | 0.71 (0.43, 1.16) |
| Insulin | | | | p = 0.6832[3] |
| No | Placebo | 3405 | 42 (1.2%) | |
| | NB | 3404 | 24 (0.7%) | 0.55 (0.33, 0.92) |
| Yes | Placebo | 1045 | 17 (1.6%) | |
| | NB | 1051 | 11 (1.0%) | 6.67 (0.31, 1.43) |
| Thiazolidinediones | | | | p = 0.6905[3] |
| No | Placebo | 4097 | 56 (1.4%) | |
| | NB | 4131 | 33 (0.8%) | 0.57 (0.37, 0.88) |
| Yes | Placebo | 353 | 3 (0.8%) | |
| | NB | 324 | 2 (0.6%) | 0.84 (0.14, 5.00) |
| Metformin | | | | p = 0.2301[3] |
| No | Placebo | 1584 | 31 (2.0%) | |
| | NB | 1633 | 14 (0.9%) | 0.44 (0.24, 0.83) |
| Yes | Placebo | 2866 | 28 (1.0%) | |
| | NB | 2822 | 21 (0.7%) | 0.75 (0.42, 1.32) |
| GLP-I/DPP-IV | | | | p = 0.2528[3] |
| No | Placebo | 3538 | 47 (1.3%) | |
| | NB | 3515 | 31 (0.9%) | 0.65 (0.41, 1.03) |
| Yes | Placebo | 912 | 12 (1.3%) | |
| | NB | 940 | 4 (0.4%) | 0.33 (0.11, 1.02) |
| Sulfonylurea | | | | p = 0.5660[3] |
| No | Placebo | 3276 | 43 (1.3%) | |
| | NB | 3229 | 27 (0.8%) | 0.63 (0.39, 1.02) |
| Yes | Placebo | 1174 | 16 (1.4%) | |
| | NB | 1226 | 8 (0.7%) | 0.47 (0.20, 1.11) |
| Lipid Altering Medication Use | | | | p = 0.6694[3] |
| No | Placebo | 525 | 8 (1.5%) | |
| | NB | 504 | 5 (1.0%) | 0.74 (0.24, 2.27) |
| Yes | Placebo | 3925 | 51 (1.3%) | |
| | NB | 3951 | 30 (0.8%) | 0.57 (0.36, 0.90) |
| Statins | | | | p = 0.8030[3] |
| No | Placebo | 882 | 10 (1.1%) | |
| | NB | 865 | 6 (0.7%) | 0.66 (0.24, 1.81) |
| Yes | Placebo | 3568 | 49 (1.4%) | |
| | NB | 3590 | 29 (0.8%) | 0.57 (0.36, 0.91) |
| Antidepressant Medication Use | | | | p = 0.7551[3] |
| No | Placebo | 3378 | 45 (1.3%) | |
| | NB | 3355 | 26 (0.8%) | 0.56 (0.35, 0.92) |
| Yes | Placebo | 1072 | 14 (1.3%) | |
| | NB | 1100 | 9 (0.8%) | 0.66 (0.28, 1.52) |
| Selective Serotonin Reuptake Inhibitor | | | | p = 0.6977[3] |
| No | Placebo | 3779 | 49 (1.3%) | |
| | NB | 3735 | 30 (0.8%) | 0.61 (0.38, 0.96) |
| Yes | Placebo | 671 | 10 (1.5%) | |
| | NB | 720 | 5 (0.7%) | 0.48 (0.16, 1.41) |
| Duration of T2DM Category[4] | | | | p = 0.0182[3] |
| <6 years | Placebo | 1561 | 18 (1.2%) | |
| | NB | 1494 | 4 (0.3%) | 0.24 (0.08, 0.70) |
| ≥6 years | Placebo | 2166 | 25 (1.2%) | |
| | NB | 2205 | 24 (1.1%) | 0.93 (0.53, 1.64) |

TABLE 8-continued

Incidence of First MACE by Subgroup: ITT Population

| Subgroup | Treatment | N | n (%) | HR (95% CI)[1] |
|---|---|---|---|---|
| Renal Impairment Category[4] | | | | p = 0.7984[3] |
| <90 mL/min | Placebo | 1174 | 21 (1.8%) | |
| | NB | 1220 | 13 (1.1%) | 0.63 (0.31, 1.26) |
| ≥90 mL/min | Placebo | 3275 | 38 (1.2%) | |
| | NB | 3234 | 22 (0.7%) | 0.56 (0.33, 0.96) |

Abbreviations:
ACEI = angiotensin-converting enzyme inhibitors;
ARB = angiotensin II receptor blocker;
BMI = body mass index;
CI = confidence interval;
CV = cardiovascular;
DPP-IV = dipeptidyl peptidase IV;
GLP-1 = glucagon-like peptide 1;
HbA1c = hemoglobin A1c;
HR = hazard ratio;
N/A = not applicable;
NB = naltrexone SR 32 mg/bupropion SR 360 mg;
T2DM = type 2 diabetes mellitus.
[1]Based on Cox proportional hazards model; factors and covariates used to calculate the HR and 95% CI for each subgroup are summarized in the source tables.
[2]The subgroup analysis excludes subjects with no CV disease and no T2DM.
[3]Likelihood ratio-test for comparing the model with treatment*subgroup interaction term and without interaction term.
[4]The subgroup analysis excludes subjects with unknown status.

Secondary MACE Measures

The results of the secondary endpoints of four-point expanded MACE, CV death, MI, and stroke were consistent with the primary endpoint; each had a HR<1.0 and upper bound of the 95% CI<2.0. The secondary MACE measures are described in more detail in the following subsections.

Time to First Four-Point Expanded MACE

Four-point expanded MACE includes adjudicated outcomes of CV death, nonfatal MI, nonfatal stroke, and nonfatal HUSA. The incidence of first four-point expanded MACE for the ITT Population is presented in Table 9. The HR (95% CI) was 0.80 (0.57, 1.11) and 1.02 (0.66, 1.58) for the ITT and PP Populations, respectively, indicating that an excess risk of four-point expanded MACE has been excluded at the time of the analysis. The incidence of HUSA, the only term not included for the primary endpoint, was numerically higher for the NB treatment group for both populations but was not associated with an increase in coronary revascularization procedures. The first occurrence of HUSA discussed below (Other Cardiovascular and All-Cause Mortality Endpoints). Separation of the four-point expanded MACE endpoint results by treatment for the ITT Population occurred by Week 24 and was favorable for NB for the remainder of the assessment period (FIG. 4). The proportion of subjects with four-point expanded MACE was similar between groups for the PP Population throughout the treatment period.

TABLE 9

Incidence of First Four-Point Expanded MACE

| | ITT Population | |
|---|---|---|
| | Placebo (N = 4450) | NB (N = 4455) |
| Four-Point Expanded MACE, n (%) of Subjects | 79 (1.8%) | 63 (1.4%) |
| CV Death | 15 (0.3%) | 4 (<0.1%) |
| Nonfatal MI | 31 (0.7%) | 23 (0.5%) |
| Nonfatal Stroke | 10 (0.2%) | 7 (0.2%) |
| Nonfatal HUSA | 23 (0.5%) | 29 (0.7%) |

TABLE 9-continued

Incidence of First Four-Point Expanded MACE

| | ITT Population | |
|---|---|---|
| | Placebo (N = 4450) | NB (N = 4455) |
| Total Subject-years at Risk | 4745.1 | 4750.7 |
| HR (95% CI)[1] | | 0.80 (0.57, 1.11) |
| p-value[2] | | <0.0001 |

Abbreviations:
CI = confidence interval;
CV = cardiovascular;
HR = hazard ratio;
HUSA = hospitalization due to unstable angina;
MACE = major adverse cardiovascular events;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥2 vs. one-sided alternative.

Time to Cardiovascular Death

The CV death endpoint includes adjudicated outcomes of sudden cardiac death, fatal MI, fatal stroke, and other fatal CV causes. The incidence of CV death for the ITT Population are presented in Table 10. The HR (95% CI) was 0.26 (0.10, 0.70) and 0.56 (0.16, 1.94) for the ITT and PP Populations, respectively, indicating that an excess risk of CV death has been excluded at the time of the analysis. Sudden cardiac death and other fatal CV causes were the primary contributors to the endpoint. Separation of the CV death endpoint results by treatment for the ITT and PP Populations occurred by Week 20 and was favorable for NB for the remainder of the assessment period (FIG. 5).

TABLE 10

Incidence of Cardiovascular Death

| | ITT Population | |
|---|---|---|
| | Placebo (N = 4450) | NB (N = 4455) |
| CV Death, n (%) of Subjects | 19 (0.4%) | 5 (0.1%) |
| Sudden Cardiac Death | 8 (0.2%) | 3 (<0.1%) |
| Fatal MI | 3 (<0.1%) | 1 (<0.1%) |
| Fatal Stroke | 1 (<0.1%) | 0 |
| Other Fatal CV Causes | 7 (0.2%) | 1 (<0.1%) |
| Total Subject-years at Risk | 4782.3 | 4787.5 |
| HR (95% CI)[1] | | 0.26 (0.10, 0.70) |
| p-value[2] | | <0.0001 |

Abbreviations:
CI = confidence interval;
CV = cardiovascular;
HR = hazard ratio;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥2 vs. one-sided alternative.

Time to First Myocardial Infarction

The MI endpoint includes adjudicated outcomes of fatal and nonfatal MI. The incidence of first MI for the ITT Population is presented in Table 11. The HR (95% CI) was 0.70 (0.42, 1.19) and 0.83 (0.40, 1.71) for the ITT and PP Populations, respectively, indicating that an excess risk of MI has been excluded at the time of the analysis. Throughout the study, the risk of MI with NB was either favorable or similar to placebo for the ITT and PP Populations (FIG. 6).

TABLE 11

Incidence of First Myocardial Infarction

| | ITT Population | |
|---|---|---|
| | Placebo (N = 4450) | NB (N = 4455) |
| MI, n (%) of Subjects | 34 (0.8%) | 24 (0.5%) |
| Nonfatal MI | 33 (0.7%) | 23 (0.5%) |
| Fatal MI | 1 (<0.1%) | 1 (<0.1%) |
| Total Subject-years at Risk | 4763.1 | 4773.2 |
| HR (95% CI)[1] | | 0.70 (0.42, 1.19) |
| p-value[2] | | <0.0001 |

Abbreviations:
CI = confidence interval;
HR = hazard ratio;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥2 vs. one-sided alternative.

Time to First Stroke

The stroke endpoint includes adjudicated outcomes of fatal and nonfatal stroke. The incidence of first stroke for the ITT Population is presented in Table 12. The HR (95% CI) was 0.63 (0.25, 1.64) for the ITT Population, indicating that an excess risk of stroke has been excluded at the time of the analysis for this population. Separation of the stroke endpoint results by treatment for the ITT Population occurred after Week 20 and was favorable for NB for the remainder of the assessment period (FIG. 7); the proportion of subjects with stroke in the PP Population was generally similar between treatment groups throughout the study.

TABLE 12

Incidence of First Stroke

| | ITT Population | |
|---|---|---|
| | Placebo (N = 4450) | NB (N = 4455) |
| Stroke, n (%) of Subjects | 11 (0.2%) | 7 (0.2%) |
| Nonfatal Stroke | 10 (0.2%) | 7 (0.2%) |
| Fatal Stroke | 1 (<0.1%) | 0 |
| Total Subject-years at Risk | 4777 | 4783.3 |
| HR (95% CI)[1] | | 0.63 (0.25, 1.64) |
| p-value[2] | | <0.0088 |

Abbreviations:
CI = confidence interval;
HR = hazard ratio;
NB = naltrexone SR 32 mg/bupropion SR 360 mg.
[1]Based on Cox proportional hazards model with treatment as a factor.
[2]p-value for testing the null hypothesis of HR ≥2 vs. one-sided alternative.

All-Cause Mortality Endpoint and Other Cardiovascular Endpoints

An overview of the all-cause mortality endpoint and other CV endpoint measures for the ITT Population is presented in Table 13. The HR (95% CI) for all-cause mortality had a point estimate favoring NB (0.45 [0.22, 0.96]). As expected given the population and study design, CV death was the primary contributor to the all-cause mortality endpoint. Separation of the all-cause mortality endpoint results by treatment for the ITT Population occurred after Week 16 and was favorable for NB for the remainder of the assessment period (FIG. 8). More subjects treated with NB experienced an endpoint event of HUSA (29, 0.7%) compared to placebo (23, 0.5%); HR (95% CI) 1.26 (0.73, 2.18). Separation of HUSA endpoint results by treatment for the ITT Population occurred early and was favorable for placebo. Importantly, this observation was not associated with an increase in coronary revascularization events (HR [95% CI] of 1.00 [0.71, 1.41]). An endpoint event of coronary revascularization procedures was experienced by 65 (1.5%) subjects in each treatment group. Throughout the study, the risk of coronary revascularization events with NB was similar to placebo for the ITT Population.

The HR (95% CI) for first five-point expanded MACE had a point estimate favoring NB (0.87 [0.65, 1.15]). Five-point expanded MACE includes adjudicated outcomes of CV death, nonfatal MI, nonfatal stroke, nonfatal HUSA, and coronary revascularization procedure. The incidence of first coronary revascularization procedure, the only term not included for four-point expanded MACE, was similar for both treatment groups (0.7% each). Separation of the five-point expanded MACE endpoint results by treatment for the ITT Population occurred by Week 24 and was favorable for NB for the remainder of the assessment period (FIG. 9). The all-cause mortality endpoint and other CV endpoint measures were also evaluated for the IT Population by CV risk group, age category, sex, race grouping, ethnicity, and BMI category.

TABLE 13

Incidence of All-Cause Mortality Endpoint and Other Cardiovascular Endpoints

| | ITT Population | |
|---|---|---|
| | Placebo (N = 4450) | NB (N = 4455) |
| All-Cause Mortality, n (%) of Subjects | 22 (0.5%) | 10 (6.2%) |

TABLE 13-continued

Incidence of All-Cause Mortality Endpoint and Other Cardiovascular Endpoints

| | ITT Population | |
|---|---|---|
| | Placebo (N = 4450) | NB (N = 4455) |
| CV Death | 19 (0.4%) | 5 (0.1%) |
| Non-CV Death | 3 (<0.1%) | 5 (0.1%) |
| Total Subject-years at Risk | 4782.3 | 4787.5 |
| HR (95% CI)[1] | | 0.45 (0.22, 0.96) |
| p-value[2] | | <0.0001 |

Abbreviations:
CI = confidence interval;
CV = cardiovascular;
HR = hazard ratio;
NB = naltrexone SR 32 mg/bupropion SR 360 mg.
[1]Based on Cox proportional hazards model with treatment as a factor.
[2]p-value for testing the null hypothesis of HR ≥2 vs. one-sided alternative.

Change in Body Weight from Baseline

Summary statistics for the percent change in body weight from baseline to Week 26 and Week 52 for the ITT (with LOCF) and PP Populations are provided in Table 14. For the ITT (with LOCF) Population, mean body weight was similar across the treatment groups at baseline (106.30 kg placebo; 105.65 kg NB). At Week 26, the LS mean percent change in body weight from baseline was statistically significantly greater with NB (−2.62%) compared to placebo (0.00%; p<0.0001); the LS mean treatment difference (NB minus placebo) was −2.63%. At Week 52, the LS mean percent change in body weight from baseline remained statistically significantly greater with NB (−2.74%) compared to placebo (0.03%; p<0.0001); the LS mean treatment difference was −2.78%.

Results from the PP Population for the LS mean treatment difference in percent change in body weight from baseline was statistically significantly greater with NB than placebo at Week 26 (−2.63%; p<0.0001) and Week 52 (−3.18%; p<0.0001) (Table 14).

TABLE 14

Percent Change in Body Weight from Baseline: ITT Population (with LOCF)

| | Placebo (N = 4450) | NB (N = 4455) |
|---|---|---|
| Baseline (kg) | | |
| n | 4449 | 4455 |
| Mean (SD) | 106.30 (19.183) | 105.65 (19.086) |
| Percent Change from Baseline to Week 2 (%) | | |
| n | 4349 | 4364 |
| Mean (SD) | −0.38 (1.429) | −0.98 (1.477) |
| LS Mean (SE) | 0.33 (0.258) | −0.26 (0.258) |
| LS Mean Diff (SE) | | −0.59 (0.031) |
| 95% CI[1] | | −0.65, −0.53 |
| p-value[1] | | <.0001 |
| Percent Change from Baseline to Week 8 (%) | | |
| n | 4370 | 4376 |
| Mean (SD) | −0.87 (2.297) | −2.62 (2.625) |
| LS Mean (SE) | 0.03 (0.436) | −1.71 (0.436) |
| LS Mean Diff (SE) | | −1.74 (0.052) |
| 95% CI[1] | | −1.84, −1.63 |
| p-value[1] | | <.0001 |
| Percent Change from Baseline to Week 16 (%) | | |
| n | 4372 | 4378 |
| Mean (SD) | −1.28 (3.169) | −3.50 (3.716) |
| LS Mean (SE) | −0.13 (0.611) | −2.33 (0.611) |
| LS Mean Diff (SE) | | −2.21 (0.073) |
| 95% CI[1] | | −2.35, −2.06 |
| p-value[1] | | <.0001 |
| Percent Change from Baseline to Week 26 (%) | | |
| n | 4372 | 4378 |
| Mean (SD) | −1.29 (3.806) | −3.93 (4.613) |
| LS Mean (SE) | 0.00 (0.747) | −2.62 (0.747) |
| LS Mean Diff (SE) | | −2.63 (0.090) |
| 95% CI[1] | | −2.80, −2.45 |
| p-value[1] | | <0.0001 |
| Percent Change from Baseline to Week 52 (%) | | |
| n | 4372 | 4378 |
| Mean (SD) | −1.23 (4.080) | −4.02 (5.233) |
| LS Mean (SE) | 0.03 (0.830) | −2.74 (0.830) |
| LS Mean Diff (SE) | | −2.78 (0.100) |
| 95% CI[1] | | −2.97, −2.58 |
| p-value[1] | | <0.0001 |

Abbreviations:
CI = confidence interval;
LOCF = last observation carried forward;
LS = least squares,
NB = naltrexone SR 32 mg/bupropion SR 360 mg,
SD = standard deviation;
SE = standard error.
[1]Based or, a general linear model with treatment, cardiovascular risk group, race grouping (white, non-white) and sex as factors, and body weight at baseline and age as covariates.

NB was statistically significantly superior to placebo (p<0.05) for the LS mean percent change in body weight from baseline to Week 52 for each subgroup examined for the ITT (with LOCF) and PP Populations. Subgroups examined included CV risk group, age category, sex, race grouping, ethnicity, and BMI category.

Note that only 44.8% of subjects had completed the Week 52 visit prior to the interim analysis cut-off date. Thus, the last observation taken at the time of the cut-off date was carried forward to Week 52 for subjects receiving medication who had not yet reached Week 52. The mean percent change in body weight from baseline over time for the ITT (with LOCF) is presented in FIG. 4. The mean percent change in body weight for the ITT (with LOCF) Population showed a larger decrease from baseline for NB over placebo at the first assessment timepoint (Week 2) and continued to separate from placebo through the first 16 weeks of treatment. The difference in mean percent change in body weight between treatment groups was generally consistent after Week 16. Overall, mean weight loss was consistently 2% to 3% greater for NB than placebo with no evidence of weight regain.

Subjects who did not meet the continuation of treatment criteria due to insufficient weight loss (or sustained increases in blood pressure) were discontinued from treatment, which is reflected in the increased rate of weight loss after Week 16 for both treatment groups for the PP Population compared to the ITT Population. The application of the Week 16 continuation of treatment criteria had a more pronounced effect on placebo than NB since a greater proportion of placebo subjects were withdrawn from study medication at that time point than NB subjects, thus diminishing the difference in weight loss between treatment groups.

Change in Systolic Blood Pressure

The mean change in systolic blood pressure from baseline by visit for the IT (with LOCF) Population is presented in FIG. 10. Note that only 44.8% of subjects had completed the Week 52 visit prior to the interim analysis cut-off date. Thus, the last observation taken at the time of the cut-off date was carried forward to Week 52 for subjects receiving medication who had not yet reached Week 52. Blood pressure changes were slightly more favorable with placebo than NB at each time point. In the placebo group, mean systolic blood pressure decreased below baseline at Week 2, then steadily increased through Week 52. In the NB group, systolic blood pressure values were approximately 0.5 mm Hg higher than placebo at most time points, which peaked at Week 8 with a treatment difference of approximately 1 mm Hg that resolved by Week 16.

Subjects who did not meet the continuation of treatment criteria due to sustained increases in blood pressure (or insufficient weight loss) were discontinued from treatment, which is reflected in a sharp decrease in the systolic blood pressure after Week 16 for both treatment groups for the PP Population compared to the ITT Population (with LOCF). Additionally, all subjects in the NB group were on treatment at each time point per the PP Population definition and under the sympathomimetic effects of bupropion, which contributed to the magnitude of the treatment difference after Week 16 compared to the ITT Population (with LOCF).

Change in Diastolic Blood Pressure

The mean change in diastolic blood pressure from baseline by visit for the ITT (with LOCF) Population is presented in FIG. 11. Note that only 44.8% of subjects had completed the Week 52 visit prior to the interim analysis cut-off date. Thus, the last observation taken at the time of the cut-off date was carried forward to Week 52 for subjects receiving medication who had not yet reached Week 52. Blood pressure changes were more favorable with placebo than NB at each time point. In the placebo group, mean diastolic blood pressure was within 1 mm Hg from baseline at each time point through Week 52. In the NB group, diastolic blood pressure values were approximately 0.5 mm Hg higher than placebo at most time points, which peaked at Week 8 with a treatment difference of approximately 1 mm Hg that resolved by Week 16.

Subjects who did not meet the continuation of treatment criteria due to sustained increases in blood pressure (or insufficient weight loss) were discontinued from treatment, which is reflected in a sharp decrease in the diastolic blood pressure after Week 16 for both treatment groups for the PP Population compared to the ITT Population (with LOCF). Additionally, all subjects in the NB group were on treatment at each time point per the PP Population definition and under the sympathomimetic effects of bupropion, which contributed to the magnitude of the treatment difference after Week 16 compared to the ITT Population (with LOCF).

Overall, the small relative increases in diastolic blood pressure with NB treatment relative to placebo in NB-CVOT are consistent with that observed in the Phase 3 program.

CONCLUSIONS

In conclusion, the favorable point estimate for the hazard ratio (HR) and upper bound of the 95% CI of less than 1.0 at the time of this interim analysis indicate that the risk of MACE in overweight and obese subjects treated with NB is not increased compared to those receiving placebo. Of note, these favorable results were observed in a population well treated according to standard of care with medications to treat diabetes, dyslipidemia, and hypertension. The point estimate for primary MACE was observed in this study (HR [95% CI]: 0.59 [0.39, 0.90]) suggests that the treatment with NB reduces the risk of MACE, rather than increasing it as anticipated by the FDA. Despite the small relative increases in blood pressure with NB treatment, which were also observed in earlier trials, the results of the MACE endpoints at the time of the interim analysis clearly suggests no harm related to the mild sympathomimetic action of NB.

While the overall patient population receiving NB had a reduced HR for MACE, several NB patient subpopulations are of particular interest because of the change in risk of MACE in these patient groups. For example, smoking status and duration of T2DM. Current smokers (HR [95% CI]: 0.10 [0.01, 0.771) and patients with T2DM less than 6 years (HR [95% CI]: 0.24 [0.08, 0.70]) showed a greater reduction in the risk of MACE compared to non-smokers (HR 195% CI]: 0.69 [0.44, 1.07]) and patients with T2DM 6 or more years (HR [95% CI]: 0.93 (0.53, 1.64)). Based on these results, overweight or obese patients at increased risk of adverse cardiovascular events who are current smokers or have T2DM less than 6 years will benefit from treatment with NB by reducing their risk of MACE compared to the general population of overweight or obese patients at increased risk of adverse cardiovascular events.

In addition, patients who are currently using GLP-1 receptor agonists or DPP-4 inhibitors demonstrated good reduction of in the risk of MACE compared to patients who are not on these medications (HR=0.33 [0.11, 1.02]). Patients who are currently not taking antidiabetic medications or metformin also showed good reduction in the risk of MACE (HR=0.37, 0.44 respectively). Patients who have a BMI of ≥35 kg/m$^2$ and <40 kg/m$^2$, male patients, patients who are over 65 years old also showed improved reduction of the risk of MACE of with HR being 0.35, 0.43 and 0.46 respectively, compared to the overall HR of 0.59.

What is claimed is:

1. A method of treating overweight or obesity in a subject having an increased risk of adverse cardiovascular outcomes, the method comprising:
   treating the subject for overweight or obesity by administering to the subject a daily dose of 4-50 mg of naltrexone, or a pharmaceutically acceptable salt thereof, and 50-400 mg bupropion, or a pharmaceutically acceptable salt thereof, for a period of at least 12 weeks.

2. The method of claim 1, wherein the subject is a current smoker that does not have type-two diabetes.

3. The method of claim 1, wherein the subject was administered:
   about 8 mg of naltrexone or a pharmaceutically acceptable salt thereof and about 90 mg of bupropion or a pharmaceutically acceptable salt thereof daily for a first week of treatment;
   about 16 mg of naltrexone or a pharmaceutically acceptable salt thereof and about 180 mg of bupropion or a pharmaceutically acceptable salt thereof daily for a second week of treatment;
   about 24 mg of naltrexone or a pharmaceutically acceptable salt thereof and about 270 mg of bupropion or a pharmaceutically acceptable salt thereof daily for a third week of treatment; and
   about 32 mg of naltrexone or a pharmaceutically acceptable salt thereof and about 360 mg of bupropion or a pharmaceutically acceptable salt thereof daily for a fourth week of treatment and any subsequent weeks of treatment.

4. The method of claim 1, wherein the period of treatment is at least 20 weeks.

5. The method of claim 2, wherein the subject was administered:
- about 8 mg of naltrexone or a pharmaceutically acceptable salt thereof and about 90 mg of bupropion or a pharmaceutically acceptable salt thereof daily for a first week of treatment;
- about 16 mg of naltrexone or a pharmaceutically acceptable salt thereof and about 180 mg of bupropion or a pharmaceutically acceptable salt thereof daily for a second week of treatment;
- about 24 mg of naltrexone or a pharmaceutically acceptable salt thereof and about 270 mg of bupropion or a pharmaceutically acceptable salt thereof daily for a third week of treatment; and
- about 32 mg of naltrexone or a pharmaceutically acceptable salt thereof and about 360 mg of bupropion or a pharmaceutically acceptable salt thereof daily for a fourth week of treatment and any subsequent weeks of treatment.

6. The method of claim 2, wherein the period of treatment is at least 20 weeks.

7. The method of claim 1, wherein the subject has type-two diabetes.

8. The method of claim 7, wherein the subject has had type-two diabetes for less than 6 years.

9. The method of claim 1, wherein the subject is a current smoker.

10. The method of claim 1, wherein the subject has a history of cardiovascular disease.

11. The method of claim 10, wherein the subject has one or more of:
- a history of documented myocardial infarction more than 3 months prior to treatment;
- a history of coronary, carotid or peripheral revascularization;
- angina with ischemic changes,
- ECG changes on a graded exercise test;
- positive cardiac imaging study;
- ankle brachial index less than 0.9 within 2 years prior to treatment; or
- greater than 50% stenosis of a coronary, carotid, or lower extremity artery within 2 years prior to treatment.

12. The method of claim 1, wherein administering the sustained release naltrexone or a pharmaceutically acceptable salt thereof and sustained release bupropion or a pharmaceutically acceptable salt thereof decreases the subject's risk of a major adverse cardiovascular outcome.

13. The method of claim 7, wherein administering the naltrexone or a pharmaceutically acceptable salt thereof and bupropion or a pharmaceutically acceptable salt thereof decreases the subject's risk of a major adverse cardiovascular outcome.

14. The method of claim 8, wherein administering the naltrexone or a pharmaceutically acceptable salt thereof and bupropion or a pharmaceutically acceptable salt thereof decreases the subject's risk of a major adverse cardiovascular outcome.

15. The method of claim 9, wherein administering the naltrexone or a pharmaceutically acceptable salt thereof and bupropion or a pharmaceutically acceptable salt thereof decreases the subject's risk of a major adverse cardiovascular outcome.

16. The method of claim 1, wherein the adverse cardiovascular outcome is selected from the group consisting of cardiovascular death, nonfatal myocardial infarction, and nonfatal stroke.

17. The method of claim 12, wherein the adverse cardiovascular outcome is selected from the group consisting of cardiovascular death, nonfatal myocardial infarction, and nonfatal stroke.

18. The method of claim 13, wherein the adverse cardiovascular outcome is selected from the group consisting of cardiovascular death, nonfatal myocardial infarction, and nonfatal stroke.

19. The method of claim 14, wherein the adverse cardiovascular outcome is selected from the group consisting of cardiovascular death, nonfatal myocardial infarction, and nonfatal stroke.

20. The method of claim 15, wherein the adverse cardiovascular outcome is selected from the group consisting of cardiovascular death, nonfatal myocardial infarction, and nonfatal stroke.

* * * * *

(12) EX PARTE REEXAMINATION CERTIFICATE (234th)
Ex Parte Reexamination Ordered under 35 U.S.C. 257

United States Patent
Klassen et al.

(10) Number: US 10,835,527 C1
(45) Certificate Issued: Nov. 14, 2023

(54) COMPOSITIONS AND METHODS FOR REDUCING MAJOR ADVERSE CARDIOVASCULAR EVENTS

(71) Applicant: Nalpropion Pharmaceuticals LLC, Morristown, NJ (US)

(72) Inventors: Preston Klassen, La Jolla, CA (US); Kristin Taylor, San Diego, CA (US)

(73) Assignee: NALPROPION PHARMACEUTICALS LLC

Supplemental Examination Request:
No. 96/000,380, Sep. 29, 2021
No. 96/000,381, Sep. 29, 2021

Reexamination Certificate for:
Patent No.: 10,835,527
Issued: Nov. 17, 2020
Appl. No.: 16/356,663
Filed: Mar. 18, 2019

Related U.S. Application Data

(63) Continuation of application No. 15/101,878, filed as application No. PCT/US2014/068527 on Dec. 4, 2014, now Pat. No. 10,231,962, which is a continuation of application No. 14/322,810, filed on Jul. 2, 2014, now Pat. No. 8,969,371.

(60) Provisional application No. 61/984,580, filed on Apr. 25, 2014, provisional application No. 61/914,938, filed on Dec. 11, 2013, provisional application No. 61/913,216, filed on Dec. 6, 2013.

(51) Int. Cl.
| | | |
|---|---|---|
| *A61K 31/485* | (2006.01) |
| *A61P 9/10* | (2006.01) |
| *A61P 43/00* | (2006.01) |
| *A61P 9/00* | (2006.01) |
| *A61P 9/06* | (2006.01) |
| *A61P 3/04* | (2006.01) |
| *A61P 3/06* | (2006.01) |
| *A61P 3/10* | (2006.01) |
| *A61P 9/12* | (2006.01) |
| *A61P 9/04* | (2006.01) |
| *A61K 9/48* | (2006.01) |
| *A61K 31/137* | (2006.01) |

(52) U.S. Cl.
CPC ............. *A61K 31/485* (2013.01); *A61K 9/48* (2013.01); *A61K 31/137* (2013.01); *A61P 3/04* (2018.01); *A61P 3/06* (2018.01); *A61P 3/10* (2018.01); *A61P 9/00* (2018.01); *A61P 9/04* (2018.01); *A61P 9/06* (2018.01); *A61P 9/10* (2018.01); *A61P 9/12* (2018.01); *A61P 43/00* (2018.01); *A61K 2300/00* (2013.01)

(58) Field of Classification Search
None
See application file for complete search history.

(56) References Cited

To view the complete listing of prior art documents cited during the supplemental examination proceedings and the resulting reexamination proceedings for Control Numbers 96/000,380 and 96/000,381, please refer to the USPTO's Patent Electronic System.

*Primary Examiner* — Jerry D Johnson

(57) ABSTRACT

The present application relates to composition kits, uses, systems and methods of using naltrexone and bupropion or pharmaceutically acceptable salts thereof, for reducing the risk of adverse cardiovascular outcomes or events, including Major Adverse Cardiovascular Events (MACE) in subjects, preferably those at increased risk of adverse cardiovascular outcomes or MACE, that may be overweight or obese. The present application also relates to compositions, kits, uses, systems and methods of using naltrexone and bupropion or pharmaceutically acceptable salts thereof for treatment of overweight or obesity in subjects, preferably at increased risk of adverse cardiovascular outcomes or MACE, wherein the treatment reduces the risk of MACE.

At the time of issuance and publication of this certificate, the patent remains subject to pending reissue application number 18/135,477 filed Apr. 17, 2023. The claim content of the patent may be subsequently revised if a reissue patent is issued from the reissue application.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*